US008501921B2

(12) United States Patent
Bamdad et al.

(10) Patent No.: US 8,501,921 B2
(45) Date of Patent: Aug. 6, 2013

(54) DETECTION OF TARGET ANALYTES USING PARTICLES AND ELECTRODES

(75) Inventors: Cynthia C. Bamdad, Sharon, MA (US); Robert C. Mucic, Glendale, CA (US)

(73) Assignee: Osmetech Technology, Inc., Carlsbad, CA (US)

( * ) Notice: Subject to any disclaimer, the term of this patent is extended or adjusted under 35 U.S.C. 154(b) by 1559 days.

(21) Appl. No.: 11/982,435

(22) Filed: Oct. 31, 2007
(Under 37 CFR 1.47)

(65) Prior Publication Data

US 2012/0135530 A1    May 31, 2012

Related U.S. Application Data

(63) Continuation of application No. 11/445,815, filed on Jun. 1, 2006, now abandoned, which is a continuation of application No. 10/016,416, filed on Dec. 10, 2001, now Pat. No. 8,012,743, which is a continuation of application No. 09/428,155, filed on Oct. 27, 1999, now Pat. No. 6,541,617.

(60) Provisional application No. 60/105,875, filed on Oct. 27, 1998.

(51) Int. Cl.
| C07H 21/02 | (2006.01) |
| C07H 21/04 | (2006.01) |
| A61K 39/395 | (2006.01) |
| A61K 39/40 | (2006.01) |
| A61K 39/42 | (2006.01) |
| A61K 39/44 | (2006.01) |
| C12Q 1/68 | (2006.01) |
| G01N 33/53 | (2006.01) |
| C12P 19/34 | (2006.01) |

(52) U.S. Cl.
USPC ... 536/23.1; 536/24.3; 536/24.33; 424/130.1; 424/178.1; 435/6.1; 435/6.11; 435/7.1; 435/91.1

(58) Field of Classification Search
USPC .............. 435/6.1, 6.11, 7.1, 91.1, 183, 283.1, 435/287.1, 287.2; 436/94, 501; 536/23.1, 536/24.3, 24.33; 530/300, 350; 424/130.1, 424/178.1, 184.1
See application file for complete search history.

(56) References Cited

U.S. PATENT DOCUMENTS

| 4,707,352 A | 11/1987 | Stavrianopoulos |
| 4,711,955 A | 12/1987 | Ward et al. |
| 4,849,513 A | 7/1989 | Smith et al. |
| 4,943,523 A | 7/1990 | Stavrianopoulos |
| 4,945,045 A | 7/1990 | Forrest et al. |
| 4,952,685 A | 8/1990 | Stavrianopoulos |
| 5,002,885 A | 3/1991 | Stavrianopoulos |
| 5,013,831 A | 5/1991 | Stavrianopoulos |
| 5,082,830 A | 1/1992 | Brakel et al. |
| 5,089,112 A | 2/1992 | Skotheim et al. |
| 5,175,269 A | 12/1992 | Stavrianopoulos |
| 5,180,968 A | 1/1993 | Bruckenstein et al. |
| 5,241,060 A | 8/1993 | Engelhardt et al. |
| 5,278,043 A | 1/1994 | Bannwarth et al. |
| 5,312,527 A | 5/1994 | Mikkelsen et al. |
| 5,328,824 A | 7/1994 | Ward et al. |
| 5,356,786 A | 10/1994 | Heller et al. |
| 5,403,451 A | 4/1995 | Riviello et al. |
| 5,449,767 A | 9/1995 | Ward et al. |
| 5,476,928 A | 12/1995 | Ward et al. |
| 5,552,270 A | 9/1996 | Khrapko et al. |
| 5,573,906 A | 11/1996 | Bannwarth et al. |
| 5,595,908 A | 1/1997 | Fawcett et al. |
| 5,601,982 A | 2/1997 | Sargent et al. |
| 5,741,700 A | 4/1998 | Ershov et al. |
| 5,756,050 A | 5/1998 | Ershov et al. |
| 5,770,721 A | 6/1998 | Ershov et al. |
| 5,776,672 A | 7/1998 | Hashimoto et al. |
| 5,823,447 A | 10/1998 | Maybach |
| 5,851,772 A | 12/1998 | Mirzabekov et al. |
| 6,002,817 A * | 12/1999 | Kopelman et al. ............... 385/12 |
| 6,008,002 A * | 12/1999 | Bodey .......................... 435/7.23 |
| 6,060,023 A | 5/2000 | Maracas |
| 6,060,327 A | 5/2000 | Keen |
| 6,107,080 A | 8/2000 | Lennox |
| 6,579,721 B1 * | 6/2003 | Natan et al. ................... 436/164 |
| 6,974,669 B2 | 12/2005 | Mirkin et al. |

FOREIGN PATENT DOCUMENTS

| CA | 2090904 | 9/1993 |
| EP | 0 63879 | 11/1982 |
| EP | 0234938 | 2/1987 |
| EP | 0 229943 | 7/1987 |
| EP | 0515615 | 9/1996 |
| JP | 238166 | 10/1988 |
| JP | 6 41183 | 2/1994 |

(Continued)

OTHER PUBLICATIONS

Stratagene Catalog (1988), p. 39. Published by Stratgene, 11011 North Torrey Pines Road, La Jolla, CA 92037, USA.*
Barisci et al., "Conducting Polymer Sensors," *TRIP*, 4(9) 307-311 (1996).
Baum, "Views on Biological, Long-Range Electron Transfer Stir Debate," *C&EN*, pp. 20-23 (1993).
Bechtold et al., "Ruthenium-Modified Horse Heart Cytochrome c: Effect of pH and Ligation on the Rate of Intramolecular Electron Transfer Between Ruthenium(II) and Heme(III)," *J. Phys. Chem.*, 90(16):3800-3804 (1986).
Biotechnology and Genetics: Genetic Screening Integrated Circuit, *The Economist* (Feb. 25-Mar. 3, 1995).

(Continued)

*Primary Examiner* — Frank Lu
(74) *Attorney, Agent, or Firm* — Morgan, Lewis & Bockius, LLP; Robin M. Silva; Gregory Ellis

(57) ABSTRACT

The invention relates to the use of particles comprising binding ligands and electron transfer moieties (ETMs). Upon binding of a target analyte, a particle and a reporter composition are associated and transported to an electrode surface. The ETMs are then detected, allowing the presence or absence of the target analyte to be determined.

4 Claims, 10 Drawing Sheets

FOREIGN PATENT DOCUMENTS

| WO | WO 90/05732 | 5/1990 |
|---|---|---|
| WO | WO 92/10757 | 6/1992 |
| WO | WO 93/10267 | 5/1993 |
| WO | WO 93/23425 | 11/1993 |
| WO | WO 94/22889 | 10/1994 |
| WO | WO 97/01646 | 1/1997 |
| WO | WO 97/27329 | 7/1997 |
| WO | WO 97/44651 | 11/1997 |
| WO | WO 98/27229 | 6/1998 |
| WO | WO 98/28444 | 7/1998 |
| WO | WO 99/14596 | 3/1999 |
| WO | WO 00/33079 A1 | 6/2000 |
| WO | WO 01/00876 A1 | 11/2001 |

OTHER PUBLICATIONS

Brun et al., "Photochemistry of Intercalated Quaternary Diazaaromatic Salts," *J. Am. Chem. Soc.*, 113:8153-8159 (1991).

Bumm et al., "Are Single Molecular Wires Conducting?," *Science* 271:1705-1707 (1996).

Cantor et al., "Report on the Sequencing by Hybridization Workshop," *Genomics*, 13:1378-1383 (1992).

Chidsey et al., "Free Energy and Temperature Dependence of Electron Transfer at the Metal Electrolyte Interface," *Science*, 251:919-923 (1991).

Clery, "DNA Goes Electric," *Science*, 267:1270 (1995).

*Commerce Business Daily Issue* of Sep. 26, 1996 PSA#1688.

Davis et al., "Electron Donor Properties of the Antitumour Drug Amsacrine as Studied by Fluorescence Quenching of DNA-Bound Ethidium,"*Chem.-Biol. Interactions*, 62:45-58 (1987).

Degani et al., "Electrical Communication Between Redox Centers of Glucose Oxidase and Electrodes via Electrostatically and Covalently Bound Redox Polymers," *J. Am. Chem. Soc.*, 111:2357-2358 (1989).

Deinhammer, et al., "Electrochemical Oxidation of Amine-Containing Compounds: A Route to the Surface Modification of Glassy Carbon Electrodes," *Langmiur*, 10:1306-1313 (1994).

Dreyer et al., "Sequence-Specific Cleavage of Single-Stranded DNA: Oligodeoxynucleotide-EDTA•Fe(II)," *Proc. Natl. Acad. Sci. USA*, 82:968-972 (1985).

Durham et al., "Photoinduced Electron-Transfer Kinetics of Singly Labeled Ruthenium Bis(bipyridin) Dicarboxy-bipyridine Cytochrome c Derivatives," *Biochemistry*, 28:8659-8665 (1989).

Elias et al., "Electron-Transfer Kinetics of Zn-Substituted Cytochrome c and Its $Ru(NH_3)_5$(Histidine-33) Derivative," *J. Am. Chem. Soc.*, 110:429-434 (1988).

Farver et al., "Long-Range Intramolecular Electron Transfer in Azurins," *Proc. Natl. Acad. Sci. USA*, 86:6968-6972 (1989).

Fox et al., "Gaussian Free-Energy Dependence of Electron-Transfer Rates in Iridium Complexes," *Science*, 247:1069-1071 (1990).

Fox et al., "Light-Harvesting Polymer Systems," *C&EN*, pp. 38-48 (Mar. 15, 1993).

Friedman et al., "Molecular 'Light Switch' for DNA: $Ru(bpy)_2(dppz)^{2+}$," *J. Am. Chem. Soc.*, 112:4960-4962 (1990).

Fromherz et al., "Photoinduced Electron Transfer in DNA Matrix from Intercalated Ethidium to Condensed Methylviologen," *J. Am. Chem. Soc.*, 108:5361-5362 (1986).

Gardner et al., "Application of Conducting Polymer Technology in Microsystems," *Sensors and Actuators*, A51:57-66 (1995).

Gregg et al., "Cross-Linked Redox Gels Containing Glucose Oxidase for Amperometric Biosensor Applications," *Anal. Chem.*, 62:258-263 (1990).

Gregg et al., "Redox Polymer Films Containing Enzymes, 1. A Redox-Conducting Epoxy Cement:: Synthesis, Characterization, and Electrocatalytic Oxidation of Hydroquinone," *J. Phys. Chem.*, 95:5970-5975 (1991).

Hashimoto et al., "Sequence-Specific Gene Detection with a Gold Electrode Modified with DNA Probes and an Electrochemically Active Dye," *Anal. Chem.* 66:3830-3833 (1994).

Heller et al., "Amperometric Biosnsors Based on Three-Dimensional Hydrogel-Forming Epoxy Networks," *Sensors and Actuators*, 13-14:180-183 (1993).

Heller et al., "Electrical Wiring of Redox Enzymes,"*Acc. Chem. Res.*, 23:128-134 (1990).

Heller et al., "Fluorescent Energy Transfer Oligonucleotide Probes," *Fed. Proc.* 46(6):1968, Abstract No. 248, (1987).

Ho, "DNA-Mediated Electron Transfer and Application to 'Biochip' Development," *Abstract Office of Naval Research* (Report Date: Jul. 25, 1991) 1-4,RR04106.

Hobbs et al., "Polynucleotides Containing 2'-Amino-2'deoxyribose and 2'-Azido-2'-deoxyriose," *Biochemistry*, 12(25):5138-5145 (1973).

Hsung et al., "Synthesis and Characterization of Unsymmetric Ferrocene-Terminated Phenylethynyl Oligomers," *Organometallics*, 14:4808-4815 (1995).

Hsung et al., "Thiophenol Protecting Groups for the Palladium-Catalyzed Heck Reaction: Efficient Syntheses of Conjugated Arylthiols," *Tetrahedron Letters*, 36(26):4525-4528 (1995).

Jenkins et al., "A Sequence-Specific Molecular Light Switch: Tebhering of an Oligonuleotide to a Dipyridophazine Complex of Ruthenium(II)," *J. Am. Chem. Soc.*, 114:8736-8738 (1992).

Katritzky et al., "Pyridylethylation—A New Protection Method for Active Hydrogen Compounds," *Tetrahedron Letters*, 25(12):1223-1226 (1984).

Kelley and Barton, "Electrochemistry of Methylene Blue Bound to a DNA-Modified Electrode," *Bioconjugated Chem*, 8:31-47 (1997).

Kojima et al., "A DNA Probe of Ruthenium Bipyridine Complex Using Photocatalytic Activity," *Chemistry Letter*, pp. 1889-1982 (1989).

Laviron, "A.C. Polarography and Faradaic Impedance of Strongly Adsorbed Electroactive Species. Part I: Theoretical Complex Plane Analysis for a Surface Redox Reaction," *J. Electroanal. Chem.*, 97:135-149 (1979).

Lee et al., "Direct Measurement of the Forces Between Complementary Strands of DNA," *Science*, 266:771-773 (1994).

Lenhard et al., "Part VII Covalent Bonding of a Reversible-Electrode Reactant to Pt Electrodes Using an Organosilane Reagent," *J. Electroanal. Chem.*, 78:195-201 (1977).

Lipkin, "Identifying DNA by the Speed of Electrons," *Science News*, 147(8):117 (1995).

Maskos et al., "Oligonucleotide Hybridizations on Glass Supports: A Novel Linke for Oligonucleotide Synthesis and Hybridization Properties of Oligonucleotides Synthesized in situ," *Nucleic Acids Research*, 20(7):1679-1684 (1992).

Mazzocchi and Fritz, Photolysis of N-(2-Methyl-2-Propenyl)phthalimide in Methanol. Evidence Supporting Radical-Radical Coupling of a Photochemically Generated Radical Ion Pair, *Journal of the American Chemical Society*, 108(18):5361-5362 (1986).

McGee et al., "2'-Amino-2'-deoxyuridine via an Intramolecular Cyclization of a Trichloroacetimidate," *J. Org. Chem.*, 61:781-785 (1996).

Mestel, "'Electron Highway' Points to Identity of DNA," *New Scientist*, p. 21 (1995).

Millan et al., "Voltammetric DNA Biosensor for Cystic Fibrosis Based on a Modified Carbon Past Electrode," *Anal. Chem.* 66:2943-2948 (1994).

Millan et al., "Covalent Immobilization of DNA onto Glassy Carton Electrodes," *Electroanalysis*, 4(10):929-932 (1992).

Millan and Mikkelsen, "Sequence-Selective Biosensor for DNA Based on Electroactive Hybridization Indicators," *Anal. Chem.*, 65:2317-2323 (1993).

Miller, "Absorbed ω-Hydroxy Thiol Monolaters on Gold Electrodes: Evidence for Electron Tunneling to Redox Species in Solution," *J. Phys. Chem*, 95:877-886 (1991).

Murphy et al., "Long-Range Photoinduced Electron Transfer Through a DNA Helix," *Science*, 262:1025-1029 (1993).

Orellana et al., "Photoinduced Electron Transfer Quenching of Excited Ru(II) Polypyridyls Bound to DNA: The Role of the Nucleic Acid Double Helix," *Photochemistry and Photobiology*, 54(4):499-509 (1991).

Palecek, "From Polarography of DNA to Micoranalysis with Nucleic Acid-Modified Electrodes," *Electroanalysis*, 8(1):7-14 (1996).

Paterson, "Electric Genes: Current Flow in DNA Could Lead to Faster Genetic Testing," *Scientific American*, 33-34 (May 1995).

Rhodes and Klug, "Helical Periodicity of DNA Determined by Enzyme Digestion," *Nature*, 286:573-578 (1980).

Risser et al., "Electron Transfer in DNA: Predictions of Exponential Growth and Decay of Coupling with Donor-Acceptor Distance," *J. Am. Chem. Soc.*, 115(6):2508-2510 (1993).

Sato et al., "Unindirectional Electron Transfer at Self-Assembled Monolayers of 11-Ferrocenyl-1-undecanethiol on Gold," *Bull. Chem. Soc. Jrn.*, 66(4):1032-1037 (1993).

Satyanarayana et al., "Neither Δ-nor A-Tris(phenanthroline)ruthenium(II) Binds to DNA by Classical Intercalation," *Biochemistry*, 31(39):9319-9324 (1992).

Schreiber et al., Bis(purine) Complees of trans-a$_2$Pt$^{11}$: Preparation and X-ray Structures of Bis(9-Methyladenine) and Mixed 9-Methyladenine, 9-Methylguanine Complexes and Chemistry Relevant to Metal-Modified Nucelobase Triples and Quartets, *J. Am. Chem. Soc.*, 118:4124-4132 (1996).

Schuhmann et al., "Electron Transfer Between Glucose Oxidase and Electrodes via Redox Mediators Bound with Flexible Chains to the Enzyme Surface," J. Am. Chem. Soc., 113:1394-1397 (1991).

Schumm et al., "Iterative Divergent/Convergent Approach to Linear Conjugated Oligomers by Successive Doubling of the Molecular Length: A Rapid Route to a 128 Å-Long Potential Molecular Wire," *Angew. Chem. Int. Ed. Engl.*, 33(11):1360-1363 (1994).

Sigal et al., "A Self-Assembled Monolayer for the Binding and Study of Histidine-Tagged Proteins by Surface Plasmon Resonance," *Anal. Chem.*, 68(3):490-497 (1996).

Southern et al., "Arrays of Complementary Oligonucleotides for Analyzing the Hybridization Behavior of Nucleic Acids," *Nucleic Acids Research*, 22(8):1368-1373 (1994).

Strobel, "Site-Specific Cleavage of a Yeast Chromosome by Oligonucleotide-Directed Triple-Helix Formation," *Science*, 249:73-75 (1990).

Su et al., "Interfacial Nucleic Acid Hybridization Studied by Random Primer $^{32}$P Labelling and Liquid-Phase Acoustic Network Analysis," *Analytical Chemistry*, 66(6):769-777 (1994).

Telser et al., "DNA Duplexes Covalently Labeled at Two Sites: Synthesis and Characterization by Steady-State and Time-Resolved Optical Spectroscopies," *J. Am. Chem. Soc.*, 111:7226-7232 (1989).

Telser et al., "DNA Oligomers and Duplexes Containing a Covalently Attached Derivative of Tris(2,2'-bipyridine)ruthenium(II): Synthesis and Characterization by Thermodynamic and Optical Spectroscopic Measurements," *J. Am. Chem. Soc.*, 111:7221-7226 (1989).

Tour, "Conjugated Macromolecules of Precise Length and Constitution. Organic Synthesis for the Construction of Nanoarchitectures," *Chem. Rev.*, 96:537-554 (1996).

Tour et al., "Self-Assembled Monolayers and Multilayers of Conjugated Thiols, α-ω- Dithiols, and Thioacetyl-Containing Adsorbates. Understanding Attachments Between Potential Molecular Wires and Gold Surfaces," *J. Am. Chem. Soc.*, 117:9529-9534 (1995).

Tullis and Dombroski, "Iron(II) EDTA Used to Measure the Helical Twist Along Any DNA Molecule," *Science*, 230:679-681 (1985).

Turro et al., "Photoelectron Transfer Between Molecules Adsorbed in Restricted Spaces," *Photochem. Convers. Storage Sol. Energy, Proc. Int. Conf., 8th*, pp. 121-139 (1990).

Turro et al., "Molecular Recognition and Chemistry in Restricted Reaction Spaces. Photophysics and Photoinduced Electron Transfer on the Surfaces of Micelles, Dendrimers, and DNA," *Acc. Chem. Res.*, 24:332-340 (1991).

Van Ness et al., "A Versatile Solid Support System for Oligodeoxynucleotide Probe-Based Hybridization Assays," *Nucleic Acids Research*, 19(12):3345-3349 (1991).

Weber et al., "Voltammetry of Redox Active Groups Irreversibly Adsorbed onto Electrodes. Treatment Using the Marcus Relation Between Rate and Overpotential," *Anal. Chem.*, 66:3164-3172 (1994).

Williams et al., "Studies of Oligonucleotide Interactions by Hybridization to Arrays: The Influence of Dangling Ends on Duplex Yield," *Nucleic Acids Research*, 22(8):1365-1367 (1994).

Winkler et al., "Electron Transfer in Ruthenium-Modifier Proteins," *Chem. Rev.*, 92:369-379 (1992).

Xu et al., "Immobilization of DNA on an Aluminum(III) Alkanebisphosphonate Thin Film with Electrogenerated Chemiluminescent Detection," *J. Am. Chem. Soc.*, 116:8386-8387 (1994).

Xu et al., "Immobilization and Hybridization of DNA on an Aluminum(III) Alkanebisphosphonate Thin Film with Electrogenerated Chemiluminescent Detection," *J. Am. Chem. Soc.*, 117:2627-2631 (1995).

Yang et al., "Growth and Characterization of Metal(II) Alkaneobisphosphonate Multilayer Thin Films on Gold Surfaces," *J. Am. Chem. Soc.*, 115:11855-11862 (1993).

Zhou et al., "Fluorescent Chemosensors Based on Energy Mogration in Conjugated Polymers: The Molecular Wire Approach to Increased Sensitivity," *J. Am. Chem. Soc.*, 117:12593-12602 (1995).

Mucic et al., "Synthesis and Characterization of DNA with Ferrocenyl Groups Attached to Their 5'-Termini: Electrochemical Characterization of a Redox-Active Nucleotide Monolayer," *Chem. Commun.*, pp. 555-557 (1996).

Carr et al., "Novel Electrochemical Sensors for Neutral Molecules," *Chem. Commun.*, 1649-1650 (1997).

Carter et al., "Voltammetric Studies of the Interaction of Metal Chelates with DNA. 2. Tris-Chelated Complexes of Cobalt(III and Iron(II) with 10-Phenanthroline and 2,2'-Bi-pyridine," *J. Am. Chem. Soc.*, 11:8901-8911 (1989).

Johnston et al., "Trans-Dioxorhenium(V)-Mediated Electrocatalytic Oxidation of DNA at Indium Tin-Oxide Electrodes: Voltammetric Detection of DNA Cleavage in Solution," *Inorg. Chem.*, 33:6388-6390 (1994).

Korri-Youssoufi et al., Toward Bioelectronics: Specific DNA Recognition Based on an Oligonucleotide-Functionalized Polypyrrole, *J. Am. Chem. Soc.*, 119(31):7388-7389 (1997).

Reimers et al., "Toward Efficient Molecular Wires and Switches: The Brooker Ions," *Biosystems*, 35:107-111 (1995).

Albers et al., "Design of Novel Molecular Wires for Realizing Long-Distance Electron Transfer," *Biochemistry and Bioenergetics*, 42:25-33 (1997).

Lincoln et al., "Shorting Circuiting the Molecular Wire," *J. Am. Chem. Soc.*, 119(6):1454-1455 (1997).

Velev et al., "In Situ Assembly of Colloidal Particles Into Miniaturized Biosensors," *The ACS Journal of Surfaces and Colloids, Langmuir*, 15(11):3693-3698 (1999).

Blonder et al., "Three-Dimensional Redox-Active Layered Composites of Au-Au, Ag-Ag and Au-Ag Colloids," *Chem. Commun.* 1393-1394 (1998).

Mirkin et al., A DNA-Based Method for Rationally Assembling Nanoparticles into Macroscopic Materials,: *Nature*, 382:607-609 (1996).

Elghanian et al., "Selective Colorimetric Detection of Polynucleotides Based on the Distance-Dependent Optical Properties of Gold Nanoparticles," *Science*, 277:1078-1081 (1997).

Watson et al., "Hybrid Nanoparticles with Block Copolymer Shell Structures," *J. Am. Chem. Soc.*, 121:462-463 (1999).

Mucic et al., "DNA-Directed Synthesis of Binary Nanoparticle Network Materials," *J. Am. Chem. Soc.*, 120:12674-12675 (1998).

Mitchell et al., "Programmed Assembly of DNA Functionalized Quantum Dots," *J. Am. Chem. Soc.*, 121:8122-8123 (1999).

Kamat et al., *J. Phys. Chem.*, 93(4):1405-1409 (1989). Abstract.

Fotin et al., "Parallel Thermodynamic Analysis of Duplexes on Oligodeoxyribonucleotide Microchips," *Nucleic Acids Research*, 216(6):1515-1521 (1998).

Guschin, et al., "Manual Manufacturing of Oligonucleotide, DNA, and Protein Microchips," *Analytical Biochemistry*, 250:203-211 (1997).

Dubiley et al., "Fractionation, Phosphorylation and Ligation on Oligonucleotide Microchips to Enhance Sequencing by Hybridization," *Nucleic Acids Research*, 25(12):2259-2265 (1997).

Guschin et al., "Oligonucleotide Microchips as Genosensors for Determinative and Environmental Studies in Microbiology," *Environ. Microbiol.* 63(6):2397-2402 (1997).

Drobyshev et al., "Sequence Analysis by Hybridization with Oligonucleotide Microchip: Identification of β-thalassemia Mutations," *Gene*, 188:45-52 (1997).

Proudnikov et al., "Chemical Methods of DNA and RNA Fluorescent Labeling," *Nucleic Acids Research*, 24(22):4535-4542 (1996).

Timofeev, et al., "Methidium Intercalator Inserted into Synthetic Oligonuleotides," *Tetrahedron Letters*, 37(47):8467-8470 (1996).

Livshits et al., "Theoretical Analysis of the Kionetics of DNA Hybridization with Gel-Immobilized Oligonucleotides," *Biophysical Journal*, 71:2795-2801 (1996).

Timofeev et al., "Regioselective Immobilization of Short Oligonucleotides to Acrylic Copolymer Gel," *Nucleic Acids Research*, 24(16):3142-3148 (1996).

Parinov, "DNA Sequencing by Hybridization to Microchip octa- and Decanucleotides Extended by Stacked Pentanucleotides," *Nucleic Acid Research*, 24(15):2998-3004 (1996).

Yershov et a., "DNA Analysis and Diagnostics on Oligonucleotide Microchips," *Proc. Natl. Acad. Sci.USA*, 93:4913-4918 (1996).

Mirzabekov et al., "DNA Sequencing by Hybridization—a Megasequencing Method and a Diagnostic Tool," *Trends Biotechnol*, 12:27-32 (1994).

Brodolin et al., "Conformational Changes in *E. Coli* RNA Polymerase During Promoter Recognition," *Nucleic Acids Research*, 24(24):5748-5753 (1993).

Proudnikov, "Immobilization of DNA in Polyacrylamide Gel for the Manufacture of DNA and DNA-Oligonucleotide Microchips," *Analytical Biochemistry*, 259:34-41 (1998).

Esipova et al., "Investigation of Sites of Strong DNA-protein Interactions in DNA-Binding Proteins by Theoretical and DNA-Protein Cross-Linking Methods," *Journal of Biomolecular Structure & Dynamics*, 12(6):A049 (1995).

Sloop et al., "Metalloorganic Labels for DNA Sequencing and Mapping," *New J. Chem.*, 18:317-326 (1994).

Taton et a., "Scanometric DNA Array Detection with Nanoparticle Probes," *Science*, 289:1757-1760 (2000).

Demers et al., "A Fluorescence-Based Methods for Determining the Surface Coverage and Hybridization Efficiency of Thiol-Capped Oligonucleotides Bound to Gold Thin Films and Nanoparticles," *Analytical Chemistry*, 72(22):5535-5541 (2000).

Park et al., "The Electrical properties of Gold Nanoparticle Assemblies Linked by DNA," *Angew. Chem. Int. Ed.* 39(21):3845-3848 (2000).

Letsinger et al., "Use of a Steroid Cyclic Disulfide Anchor in Constructing Gold Nanoparticle-Oligonucleotide Conjugates," *Bioconjugate Chem*, 11:289-291 (2000).

Taton et al., "Two-Color Labeling of Oligonucleotide Arrays via Size-Selective Scattering of Nanoparticle Probes," *J. Am. Chem. Soc.*, 123:5164-5165 (2001).

Arkin et al., "Evidence for Photoelectronic Transfer Through DNA Intercalation," *J. Inorganic Biochem. Abstracts, 6th International Conference on Bioinorganic Chemistry*, 51(1): & (2):526 (1993).

Boguslavsku et al., "Application of Redox Polymers in Biosensors," *Solid State Ionics*, 60:189-197 (1993).

Laviron, "A.D. Polarography and Faradaic Impedance of Strongly Adsorbed Electroactive Species. Part III: Theoretical Complex Plane Analysis for a Surface Redox Reaction," . *Electroanal. Chem.*, 105:34-42 (1979).

\* cited by examiner

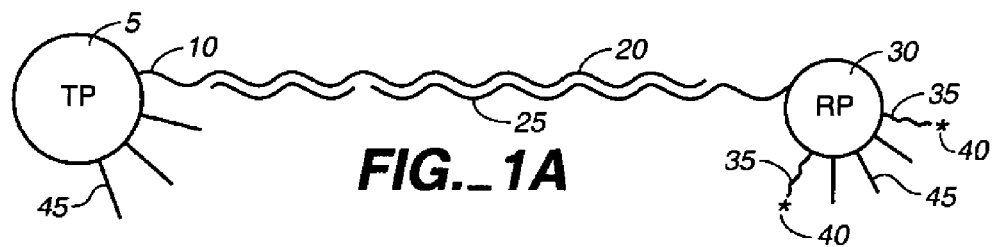
FIG._1A
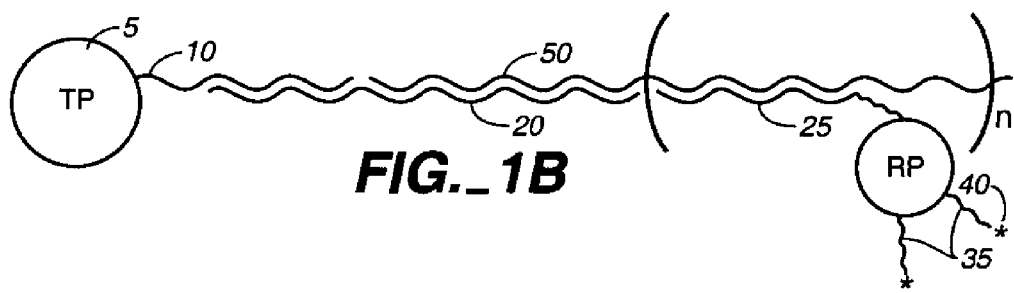
FIG._1B
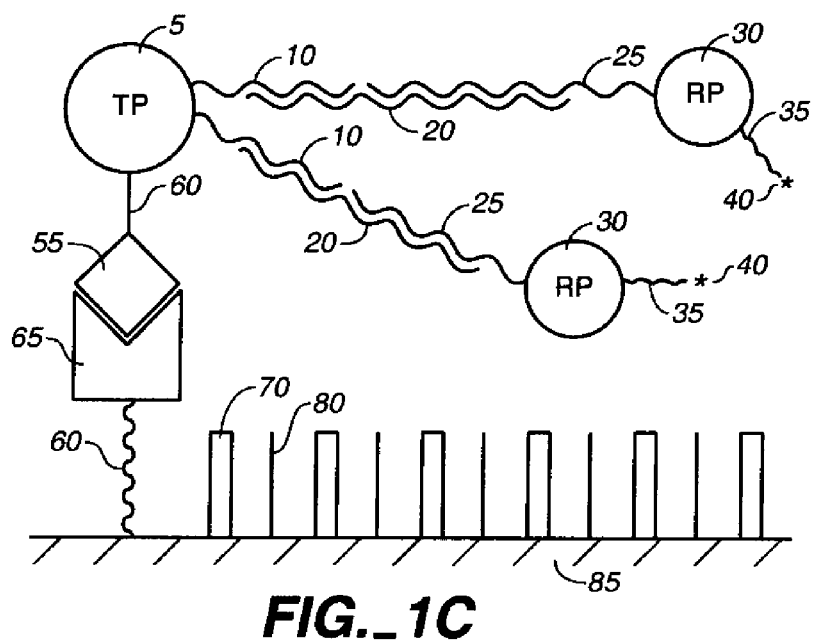
FIG._1C
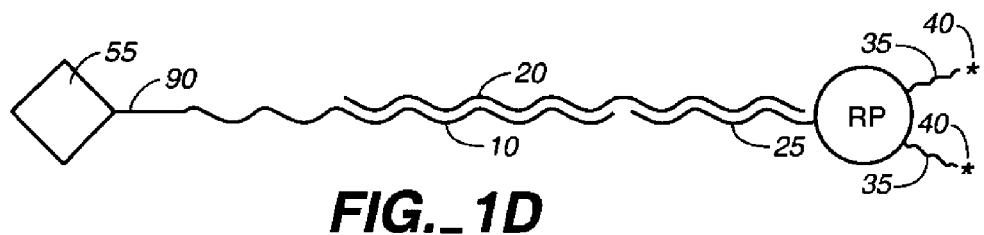
FIG._1D

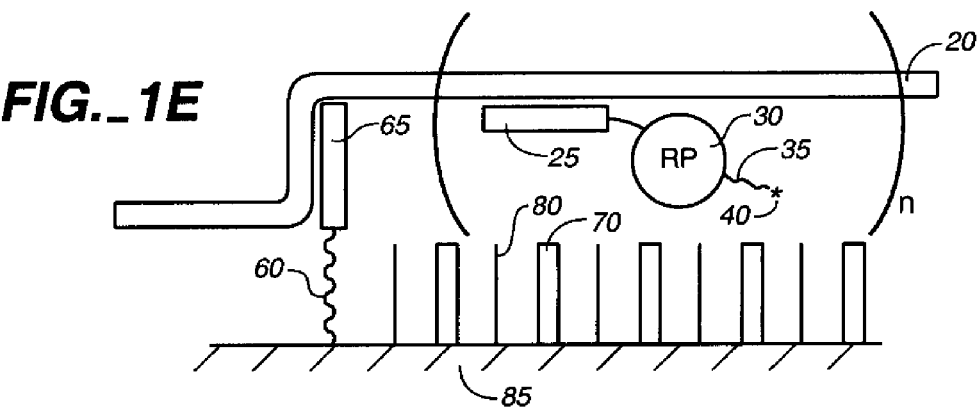
FIG._1E
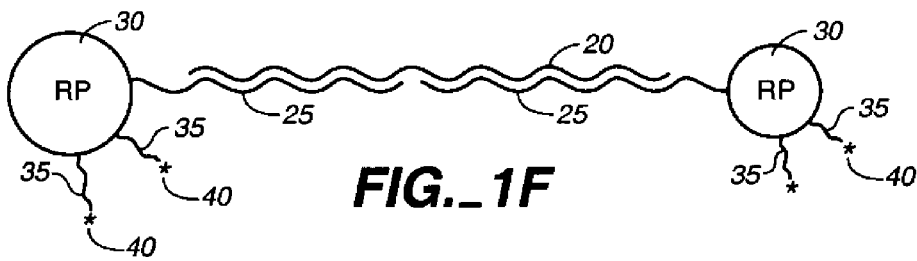
FIG._1F
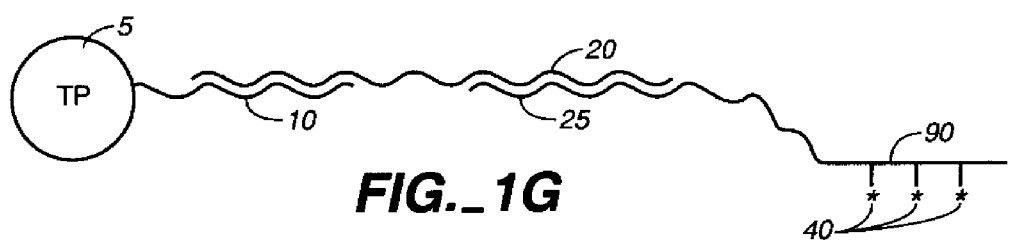
FIG._1G
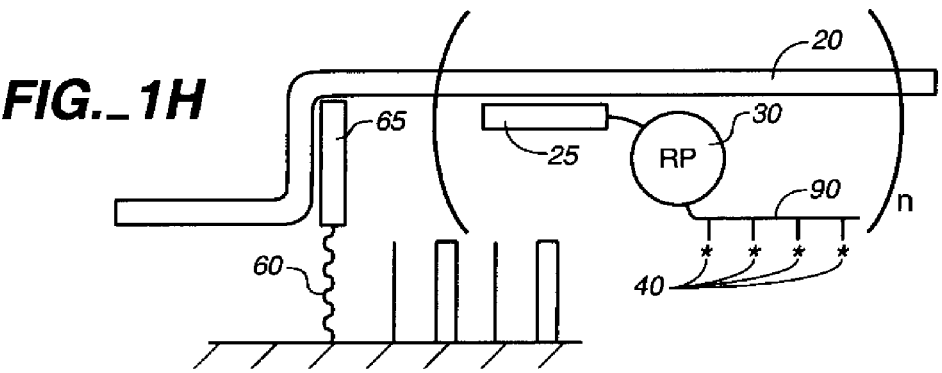
FIG._1H

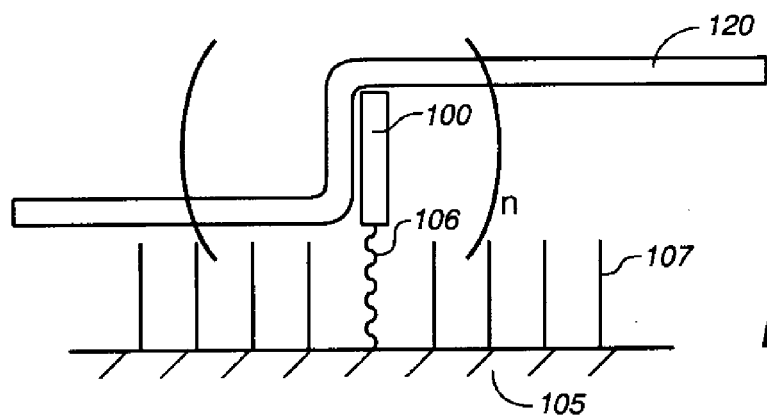
FIG._2A
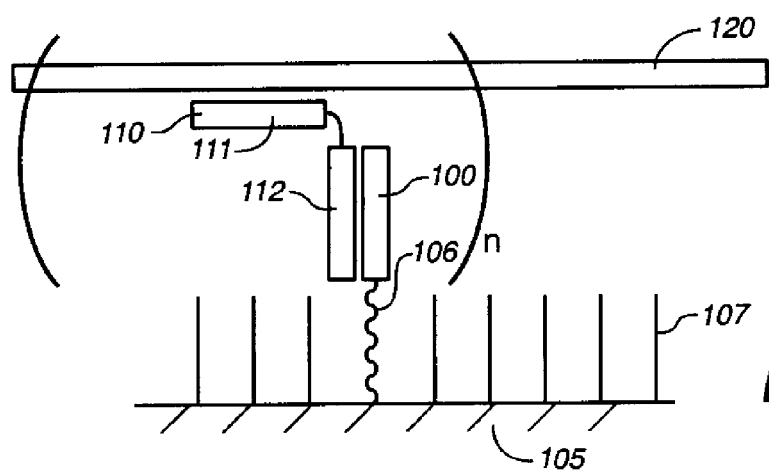
FIG._2B
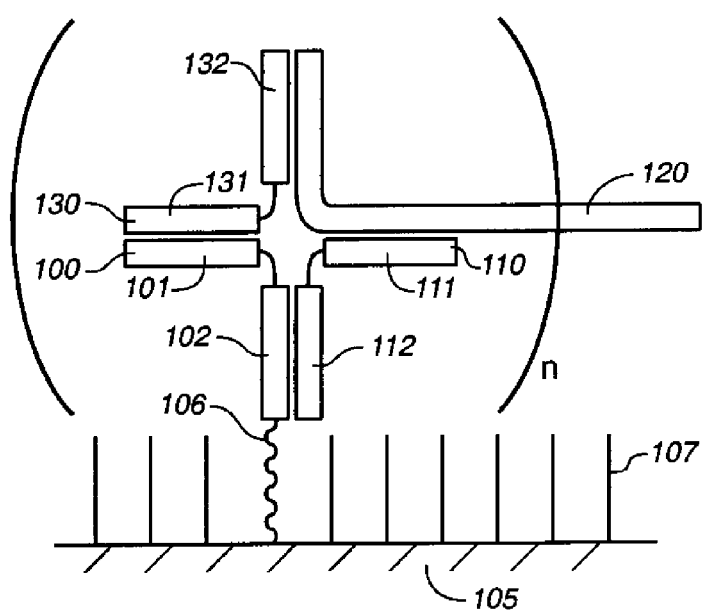
FIG._2C

A = NUCLEOSIDE REPLACEMENT
B = ATTACHMENT TO A BASE
C = ATTACHEMENT TO A RIBOSE
D = ATTACHMENT TO A PHOSPHATE
E = METALLOCENE POLYMER, ATTACHED TO A RIBOSE, PHOSPHATE, OR BASE
F = DENDRIMER STRUCTURE, ATTACHED VIA A RIBOSE, PHOSPHATE OR BASE

G = ATTACHMENT VIA A "BRANCHING STRUCTURE", THROUGH RIBOSE, PHOSPHATE OR BASE

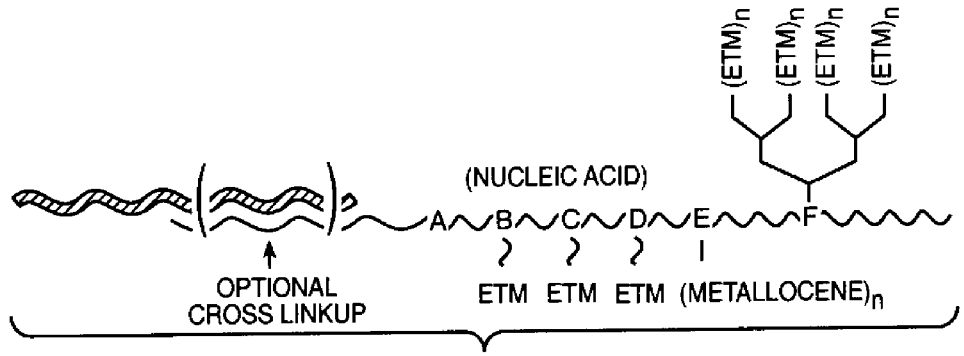
FIG._3C
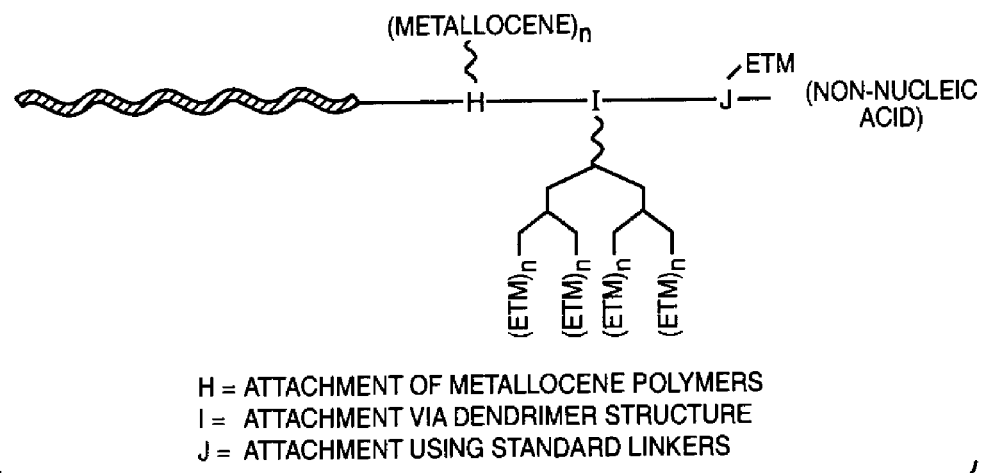
H = ATTACHMENT OF METALLOCENE POLYMERS
I = ATTACHMENT VIA DENDRIMER STRUCTURE
J = ATTACHMENT USING STANDARD LINKERS
FIG._3D
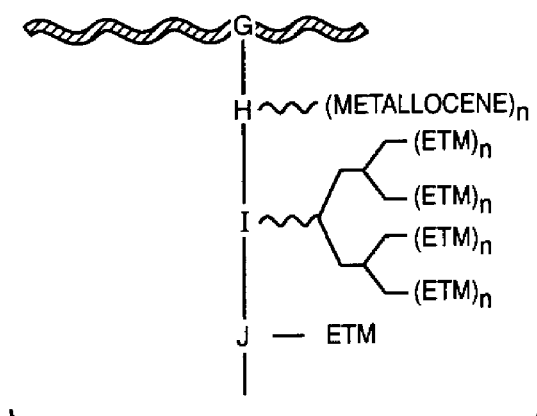
FIG._3E

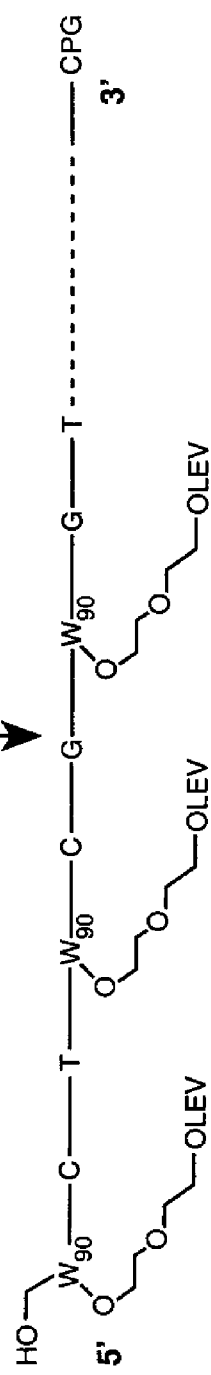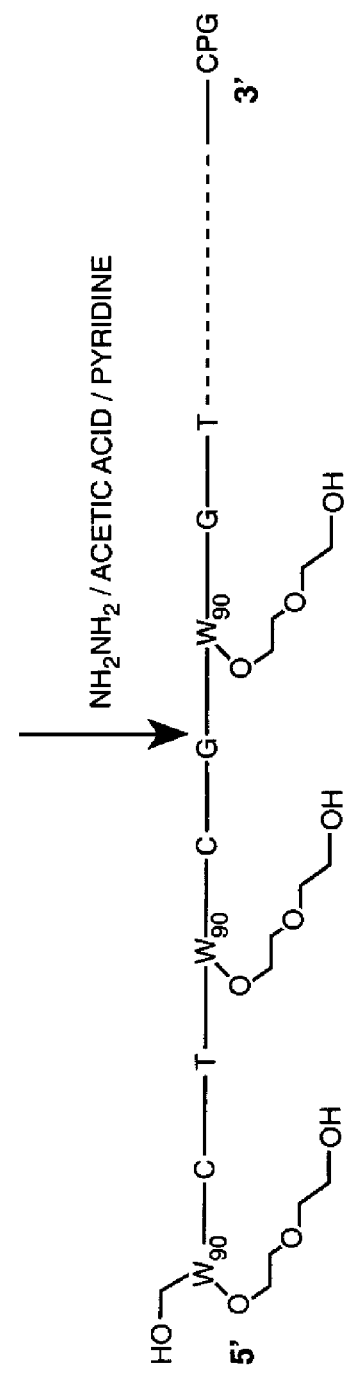
FIG._4A

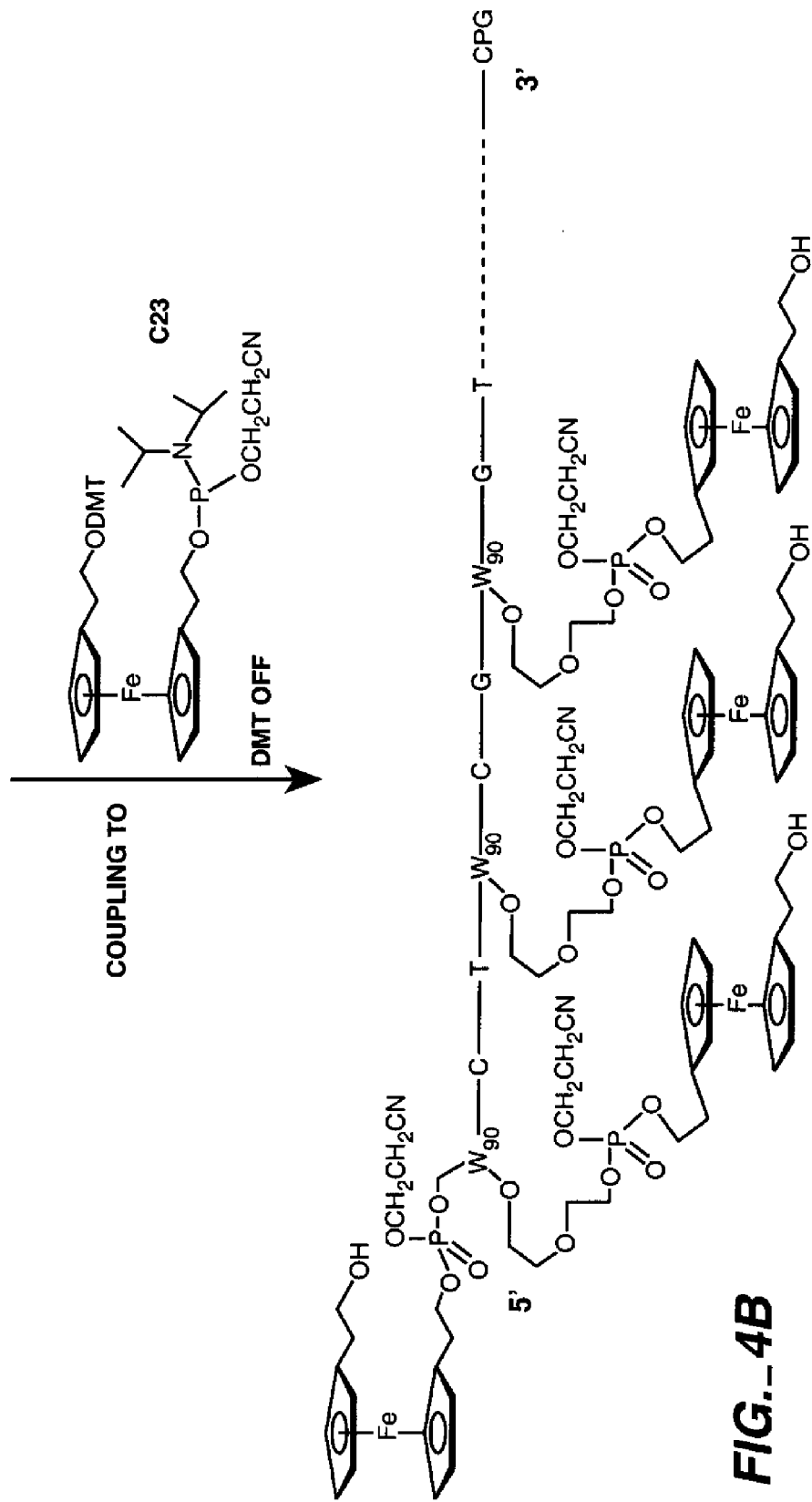
FIG._4B

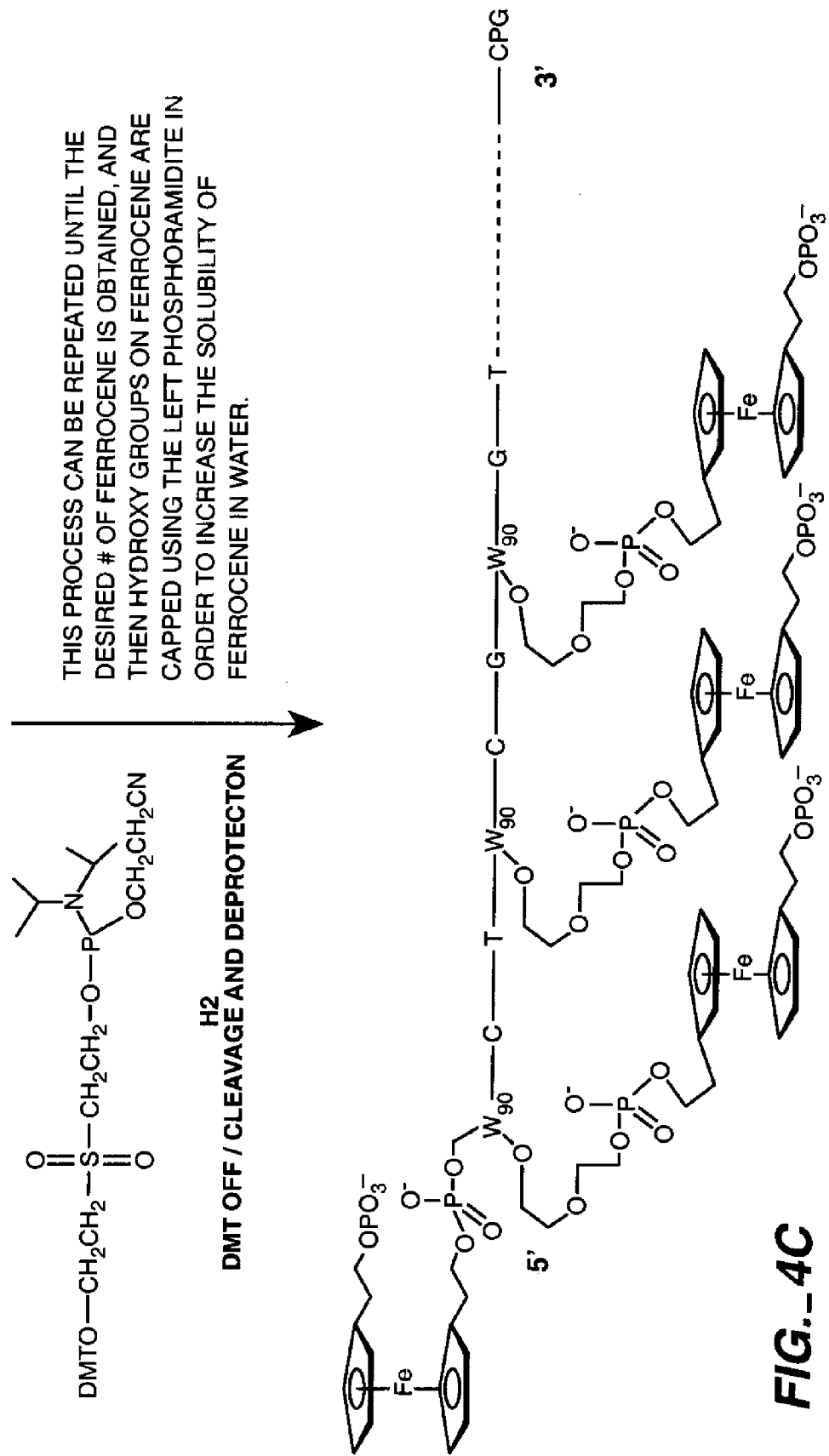
FIG._4C

FIG._5
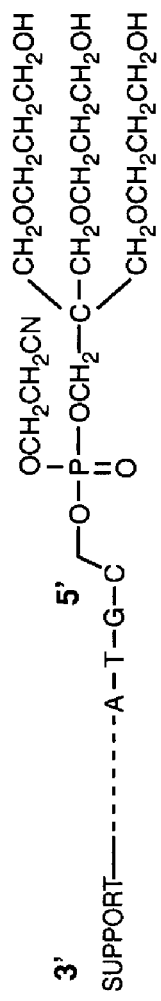
FIG._5A
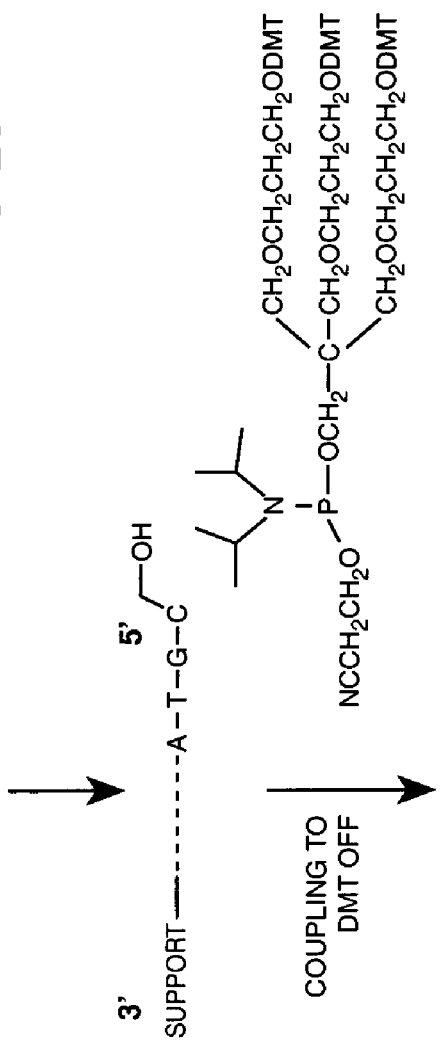

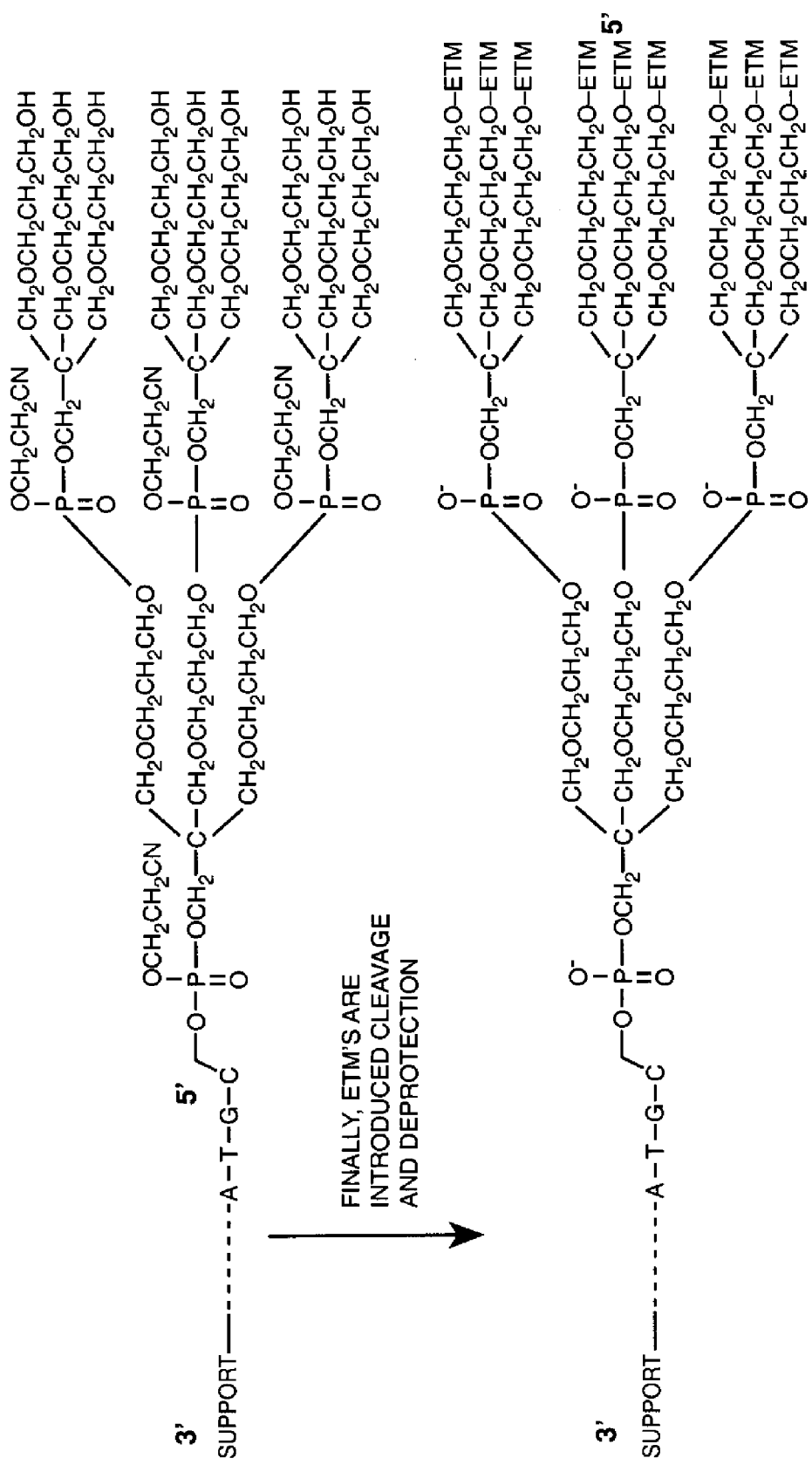
FIG._5B

DETECTION OF TARGET ANALYTES USING PARTICLES AND ELECTRODES

FIELD OF THE INVENTION

The invention relates to the use of particles comprising binding ligands and electron transfer moieties (ETMs). Upon binding of a target analyte, a particle and a reporter composition are associated and transported to an electrode surface. The ETMs are then detected, allowing the presence or absence of the target analyte to be determined.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radidisotopes, fluorescent and other optically active molecules, enzymes, etc.

Other assays rely on electronic signals for detection. Of particular interest are biosensors. At least two types of biosensors are known; enzyme-based or metabolic biosensors and binding or bioaffinity sensors. See for example U.S. Pat. Nos. 4,713,347; 5,192,507; 4,920,047; 3,873,267; and references disclosed therein. While some of these known sensors use alternating current (AC) techniques, these techniques are generally limited to the detection of differences in bulk (or dielectric) impedance, and rely on the use of mediators in solution to shuttle the charge to the electrode.

Recently, there have been several preliminary reports on the use of very short connections between a binding ligand and the electrode, for direct detection, i.e. without the use of mediators. See Lötzbeyer et al., Bioelectrochemistry and Bioenergetics 42:1-6 (1997); Dong et al., Bioelectrochemistry and Bioenergetics 42:7-13 (1997).

In addition, there are a number of reports of self-assembled monolayers of conjugated oligomers on surfaces such as gold. See for example Cygan et al., J. Am. Chem. Soc. 120: 2721 (1998).

In addition, Charych et al. report on the direct colormetric detection of a receptor-ligand interaction using 3 bilayer assembly (Science 261:585 (1993).

PCT applications WO 95/15971, PCT/US96/09769, PCT/US97/09739, WO96/40712 and PCT/US97/20014 describe novel compositions comprising nucleic acids containing electron transfer moieties, including electrodes, which allow for novel detection methods of nucleic acid hybridization.

In addition, there are a number of sensors that rely on the use of particles, including magnetic particles, particularly for electrochemiluminescence detection. See U.S. Pat. Nos. 5,746,974; 5,770,459; 5,779,976; 4,731,337; 4,115,535; 4,777,145; 4,945,045; 4,978,610; 5,705,402; 4,910,148; 5,512,439; 5,585,241; and 5,609,907; and WO 90/14891; WO 90/05301; WO 92/14139; and WO 90/06044.

Finally, there are reports that bring particles together using nucleic acids for archetectural reasons. See Mirkin et al., Nature 382:607 (1996); Mirkin et al., Science 277:1078 (1997); Storhoff et al., J. Am. Chem. Soc. 120:1959 (1998); and WO 98/10289.

SUMMARY OF THE INVENTION

In accordance with the objects outlined above, the present invention provides compositions comprising a gold colloid particle comprising at least one ETM. The colloid can further comprise a self-assembled monolayer (SAM). The compositions can further comprise an electrode, that may also contain a SAM.

In an additional aspect, the invention provides compositions comprising gold colloid particles comprising a SAM, a capture probe, an amplification sequence; and a label probe hybridized to the amplification sequence, wherein the label probe comprises at least one covalently attached ETM.

In an additional aspect, the invention provides compositions comprising a transport composition comprising a first binding partner that directly or indirectly binds a target analyte, and a reporter composition. The reporter composition comprises a second binding partner that directly or indirectly binds the target analyte and a plurality of electron transfer moieties (ETMs). At least one of the transport and the reporter compositions is a particle. Upon introduction of the target analyte, the transport composition and the reporter composition are associated. These compositions may also comprise SAMs, and an electrode, optionally containing a SAM, can be included.

In a further aspect, the invention provides methods of detecting a target analyte in a sample. The methods comprise adding the sample to a composition as outlined above, such that the target analyte binds to the transport composition and the reporter composition to form an assay complex. The assy complex is transported to the electrode, and the presence or absence of the ETMs is detected.

BRIEF DESCRIPTION OF THE DRAWINGS

FIGS. 1A-1G depict a variety of different embodiments of the invention. Many of the figures depict nucleic acids as the binding ligands, target moieties, and extender moieties, but non-nucleic acid embodiments can also be used in a similar manner. FIG. 1A shows an assay complex comprising a transport particle 5 with a first binding ligand 10. An optional SAM of moieties 45 that can be either conductive oligomers or insulators may also be present. The target analyte 20 binds to first binding ligand 10 and the second binding ligand 25, attached to the reporter particle 30. The reporter particle 30 comprises a plurality of ETMs 40, preferably linked to the reporter particle 30 via conductive oligomers 35. A SAM of moieties 45 may also optionally be present. The binding ligands 10 and 25 can be attached via attachment linkers 60, not shown, that can be a conductive oligomer, an insulator, or other moieties, as outlined herein. FIG. 1B is similar, but utilizes an extender moiety 50; as will be appreciated by those in the art, the extender moiety 50 may also be placed between the target 20 and the first binding ligand 25. In addition, the extender moiety (sometimes referred to herein as an amplifier probe) may also contain multiple amplification sequences for attachment of reporter compositions; thus n is an integer of at least one. FIG. 1C depicts the use of a capture binding ligand 55 attached to the transport particle 5 via an attachment linker 60. Additional embodiments for the attachment of nucleic acids to the electrode surface are shown in FIG. 2. The capture binding ligand 55 binds to a capture binding partner 65 attached to electrode 85 via an attachment linker 60. The electrode comprises conductive oligomers 70 and optional insulators 80. FIG. 1D depicts the use of a non-particle transport composition comprising a capture binding ligand 55 attached via an optional linker 90 (that can be an attachment linker) to the capture binding ligand 10. FIG. 1E depicts the use of the target analyte as the capture binding moiety; the target 20 binds to the capture binding partner 65, attached to the electrode 85 via an attachment linker 60. The second binding ligand 25 binds to a portion of the target 20. Depending on the length (i.e. when the target analyte is a nucleic acid) or size of the target analyte, a plurality n of reporter compositions can be used; thus n is an integer of at least one. FIG. 1F depicts the case wherein two reporter particles are used; what is important in this embodiment is that aggregation does not occur to an appreciable extent in the absence of the target 20, and that generally the two second binding ligands 25 each recognize a different part of the target 20, such that a single target will bring together at least two reporter compositions. FIG. 1G depicts the use of a non-particle reporter composition, using a recruitment linker 90, as outlined herein. FIG. 1H depicts the use of a reporter particle 30 that has both a second binding ligand 25 and a recruitment linker 90.

FIGS. 2A, 2B and 2C depict three preferred embodiments for attaching a target sequence to the electrode. Although generally depicted as nucleic acids, non-nucleic acid embodiments are also useful. FIG. 2A depicts a target sequence 120 hybridized to a capture probe 100 linked via a attachment linker 106, which as outlined herein may be either a conductive oligomer or an insulator. The electrode 105 comprises a monolayer of passivation agent 107, which can comprise conductive oligomers (herein depicted as 108) and/or insulators (herein depicted as 109). As for all the embodiments depicted in the figures, n is an integer of at least 1, although as will be appreciated by those in the art, the system may not utilize a capture probe at all (i.e. n is zero), although this is generally not preferred. The upper limit of n will depend on the length of the target sequence and the required sensitivity. FIG. 2B depicts the use of a single capture extender probe 110 with a first portion 111 that will hybridize to a first portion of the target sequence 120 and a second portion that will hybridize to the capture probe 100. FIG. 2C depicts the use of two capture extender probes 110 and 130. The first capture extender probe 110 has a first portion 111 that will hybridize to a first portion of the target sequence 120 and a second portion 112 that will hybridize to a first portion 102 of the capture probe 100. The second capture extender probe 130 has a first portion 132 that will hybridize to a second portion of the target sequence 120 and a second portion 131 that will hybridize to a second portion 101 of the capture probe 100.

FIGS. 3A, 3B, 3C, 3D and 3E depict different possible configurations of label probes and attachments of ETMs. The figures depict a second binding ligand that is a hybridizable nucleic acid, but as will be appreciated by those in the art, the second binding ligand can be non-nucleic acid as well. In FIGS. 3A-C, the recruitment linker is nucleic acid; in FIGS. 3D and E, is not. A=nucleoside replacement; B=attachment to a base; C=attachment to a ribose; D=attachment to a phosphate; E=metallocene polymer (although as described herein, this can be a polymer of other ETMs as well), attached to a base, ribose or phosphate (or other backbone analogs); F=dendrimer structure, attached via a base, ribose or phosphate (or other backbone analogs); G=attachment via a "branching" structure, through base, ribose or phosphate (or other backbone analogs); H=attachment of metallocene (or other ETM) polymers; I=attachment via a dendrimer structure; J=attachment using standard linkers.

FIGS. 4A, 4B and 4C depict a schematic of the synthesis of simultaneous incorporation of multiple ETMs into a nucleic acid, using the N17 "branch" point nucleoside.

FIGS. 5A and 5B depict a schematic of an alternate method of adding large numbers of ETMs simultaneously to a nucleic acid using a "branch" point phosphoramidite, in this case utilizing three branch points (although two branch points are also possible; see for example FIG. 1N) as is known in the art. As will be appreciated by those in the art, each end point can contain any number of ETMs.

DETAILED DESCRIPTION OF THE INVENTION

Figure 3A:
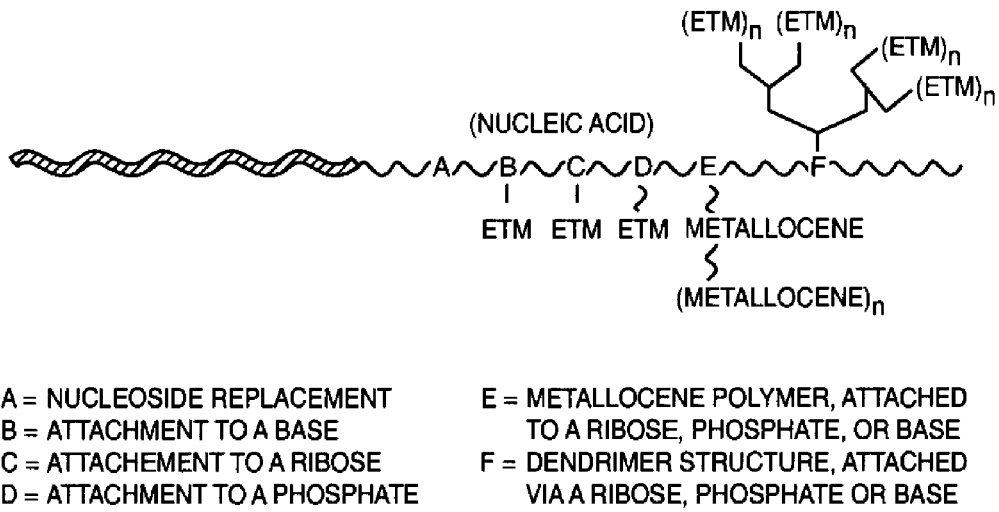

The present invention provides novel analytical biosensors that can be used to sensitively detect target analytes. In one embodiment, the system provides two basic components: (1) a first component (generally but not always a particle) that can bind a target analyte and that can be used to transport an assay complex comprising the first component to an electrode, and (2) a reporter composition (which may or may not be a particle as well) that can bind a target analyte and comprises electron transfer moieties (ETMs). The two components are brought together by the direct or indirect binding of a target analyte. That is, a single target analyte directly or indirectly binds both a first binding ligand attached to the first component and a second binding ligand attached to the reporter composition; this forms an assay complex. The first component can be used to transport the assay complex to an electrode for detection of the ETMs. This may be done in a variety of ways; for example, when the first component is a particle, transport can occur either magnetically, when the particle is a magnetic particle, or via gravity or other techniques based on the specific gravity or density of the particle in relation to the solution. In some embodiments, both components are particles and the aggregation of the particles using target analytes results in transport to the electrode. Alternatively, the first component may utilize a capture moiety for attachment to an electrode that comprises a capture binding ligand. Once the assay complexes are formed, the presence or absence of the ETMs are detected using the electrode as is described below and in U.S. Pat. Nos. 5,591,578; 5,824,473; 5,770,369; 5,705,348 and 5,780,234; U.S. Ser. Nos. 08/911,589 (now U.S. Pat. No. 6,232,062); 09/135,183 (now abandoned); 09/306,653 (now U.S. Pat. No. 6,600,026); 09/134,058 (now U.S. Pat. No. 6,290,839); 09/295,691 (now U.S. Pat. No. 6,942,771); 09/238,351 (now U.S. Pat. No. 7,090,804); 09/245,105 (now abandoned), 60/145,912 and 09/338,726 (now U.S. Pat. No. 6,264,825); and PCT applications WO 98/20162; PCT US99/01705 (now WO 99/37819); PCT US99/01703 (now WO 99/57319); PCT US99/10104 (now WO 99/57317), all of which are expressly incorporated herein by reference in their entirety.

In general, there are two basic detection mechanisms. In a preferred embodiment, detection of an ETM is based on electron transfer through the stacked π-orbitals of double stranded nucleic acid. This basic mechanism is described in U.S. Pat. Nos. 5,591,578, 5,770,369, 5,705,348, 5,824,473 and 5,780,234 and WO98/20162, all of which are expressly incorporated by reference, and is termed "mechanism-1" herein. Briefly, previous work has shown that electron transfer can proceed rapidly through the stacked π-orbitals of double stranded nucleic acid, and significantly more slowly through single-stranded nucleic acid. Accordingly, this can serve as the basis of an assay. Thus, by adding ETMs (either covalently to one of the strands or non-covalently to the hybridization complex through the use of hybridization indicators, described below) to a nucleic acid that is attached to a detection electrode via a conductive oligomer, electron transfer between the ETM and the electrode, through the nucleic acid and conductive oligomer, may be detected.

Alternatively, ETMs can be directly detected on a surface of a monolayer. That is, the electrons from the ETMs need not travel through the stacked n orbitals in order to generate a signal. As above, in this embodiment, the detection electrode preferably comprises a self-assembled monolayer (SAM) that serves to shield the electrode from redox-active species in the sample. In this embodiment, the presence of ETMs on the surface of a SAM, that has been formulated to comprise slight "defects" (sometimes referred to herein as "microconduits", "nanoconduits" or "electroconduits") can be directly detected. This basic idea is termed "mechanism-2" herein. Essentially, the electroconduits allow particular ETMs access to the surface. Without being bound by theory, it should be noted that the configuration of the electroconduit depends in part on the ETM chosen. For example, the use of relatively hydrophobic ETMs allows the use of hydrophobic electroconduit forming species, which effectively exclude hydrophilic or charged ETMs. Similarly, the use of more hydrophilic or charged species in the SAM may serve to exclude hydrophobic ETMs.

It should be noted that these defects are to be distinguished from "holes" that allow direct contact of sample components with the detection electrode. As is more fully outlined below, the electroconduits can be generated in several general ways, including but not limited to the use of rough electrode surfaces, such as gold electrodes formulated on PC circuit boards; or the inclusion of at least two different species in the monolayer, i.e. using a "mixed monolayer", at least one of which is a electroconduit-forming species (EFS). Thus, upon binding of a target analyte, a binding ligand comprising an ETM is brought to the surface, and detection of the ETM can proceed, putatively through the "electroconduits" to the electrode. Essentially, the role of the SAM comprising the defects is to allow contact of the ETM with the electronic surface of the electrode, while still providing the benefits of shielding the electrode from solution components and reducing the amount of non-specific binding to the electrodes. Viewed differently, the role of the binding ligand is to provide specificity for a recruitment of ETMs to the surface, where they can be directly detected.

Thus, in either embodiment, an assay complex is formed that contains an ETM, which is then detected using the detection electrode. The invention thus provides assay complexes that minimally comprise a target analyte. "Assay complex" herein is meant the collection of binding complexes, e.g. nucleic acids, including probes and targets, that contains at least one ETM and thus allows detection. The composition of the assay complex depends on the use of the different probe components outlined herein.

Accordingly, the present invention provides methods and compositions useful in the detection of target analytes in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705 (now WO 99/37819), such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample.

The methods are directed to the detection of target analytes. By "target analyte" or "analyte" or grammatical equivalents herein is meant any molecule or compound to be detected and that can bind to a binding species, defined below. Suitable analytes include, but not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, etc. Particularly preferred analytes are proteins including enzymes; drugs; cells; antibodies; antigens; cellular membrane antigens and receptors (neural, hormonal, nutrient, and cell surface receptors) or their ligands.

By "proteins" or grammatical equivalents herein is meant proteins, oligopeptides and peptides, and analogs, including proteins containing non-naturally occurring amino acids and amino acid analogs, and peptidomimetic structures.

As will be appreciated by those in the art, a large number of analytes may be detected using the present methods; basically, any target analyte for which a binding ligand, described below, may be made may be detected using the methods of the invention.

In a preferred embodiment, the target analytes are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed.Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and nonribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or ETM attachment, an analog structure may be used. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

Thus, in a preferred embodiment, the target analyte is a target sequence. The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction, etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art. The target sequence may also be comprised of different target domains; for example, a first target domain of the sample target sequence may hybridize to a capture probe or a portion of capture extender probe, a second target domain may hybridize to a portion of an amplifier probe, a label probe, or a different capture or capture extender probe, etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located, either 5' to the second domain, or 3' to the second domain.

In a preferred embodiment, the methods of the invention are used to detect pathogens such as bacteria. In this embodiment, preferred target sequences include rRNA, as is generally described in U.S. Pat. Nos. 4,851,330; 5,288,611; 5,723,597; 6,641,632; 5,738,987; 5,830,654; 5,763,163; 5,738,989; 5,738,988; 5,723,597; 5,714,324; 5,582,975; 5,747,252; 5,567,587; 5,558,990; 5,622,827; 5,514,551; 5,501,951; 5,656,427; 5,352,579; 5,683,870; 5,374,718; 5,292,874; 5,780,219; 5,030,557; and 5,541,308, all of which are expressly incorporated by reference.

As will be appreciated by those in the art, a large number of analytes may be detected using the present methods; basically, any target analyte for which a binding ligand, described below, may be made may be detected using the methods of the invention. While many of the techniques described below exemplify nucleic acids as the target analyte, those of skill in the art will recognize that other target analytes can be detected using the same systems.

If required, the target analyte is prepared using known techniques. For example, the sample may be treated to lyse the cells, using known lysis buffers, electroporation, etc., with purification and/or amplification as needed, as will be appreciated by those in the art. When the target analyte is a nucleic acid, the target sequence may be amplified as required; suitable amplification techniques are outlined in PCT US99/01705 (now WO 99/37819), hereby expressly incorporated by reference. In addition, techniques to increase the amount or rate of hybridization can also be used; see for example U.S. Ser. No. 09/338,726; filed Jun. 23, 1999 (now U.S. Pat. No. 6,264,825), hereby incorporated by reference.

All of these techniques rely on the formation of assay complexes on a surface, frequently an electrode, as is described herein. The assay complex preferably includes at least one particle, generally a gold colloid particle, that is used either as a transport particle or a reporter particle, or both. The assay complex further comprises at least one electron transfer moiety (ETM), that is also either directly or indirectly attached to the assay complex. Once the assay complexes are formed, the presence or absence of the ETMs are detected as is described below and in U.S. Pat. Nos. 5,591,578; 5,824,473; 5,770,369; 5,705,348 and 5,780,234; U.S. Ser. Nos. 08/911,589 (now U.S. Pat. No. 6,232,062); 09/135,183 (now abandoned); 09/306,653 (now U.S. Pat. No. 6,600,026); 09/134,058 (now U.S. Pat. No. 6,290,839); 09/295,691 (now U.S. Pat. No. 6,942,771); 09/238,351 (now U.S. Pat. No.

7,090,804); 09/245,105 (now abandoned), and 60/145,912; and PCT applications WO98/20162; PCT US99/01705 (now WO 99/37819); PCT US99/01703 (now WO 99/57319); PCT US99/14191 (now WO 99/67425); PCT US99/10104 (now WO 99/57317), all of which are expressly incorporated herein by reference in their entirety.

Accordingly, the present invention provides methods and compositions useful in the detection of target analytes, including nucleic acids. As will be appreciated by those in the art, the compositions of the invention can take on a wide variety of configurations, as is generally outlined in the Figures and described below. It should be noted that while the discussion below focuses on the detection of nucleic acids, other target analytes can be used in any of the systems described herein.

Thus, in a preferred embodiment, the compositions comprise an electrode. By "electrode" herein is meant a composition, which, when connected to an electronic device, is able to sense a current or charge and convert it to a signal. Alternatively an electrode can be defined as a composition which can apply a potential to and/or pass electrons to or from species in the solution. Thus, an electrode is an ETM as described herein. Preferred electodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the SAMs comprising conductive oligomers and nucleic acids bound to the inner surface. This allows a maximum of surface area containing the nucleic acids to be exposed to a small volume of sample.

In addition, the geometry of the system may alter with the transport mechanism used. For example, when aggregation of the particles is used to transport the ETMs to the electrode surface, the electrode surface needs to be at the bottom. However, other systems utlizing different transport mechanisms can have the electrode surface be anywhere.

In a preferred embodiment, the detection electrodes are formed on a substrate. In addition, the discussion herein is generally directed to the formation of gold electrodes, but as will be appreciated by those in the art, other electrodes can be used as well. The substrate can comprise a wide variety of materials, as will be appreciated by those in the art, with printed circuit board (PCB) materials being particularly preferred. Thus, in general, the suitable substrates include, but are not limited to, fiberglass, teflon, ceramics, glass, silicon, mica, plastic (including acrylics, polystyrene and copolymers of styrene and other materials, polypropylene, polyethylene, polybutylene, polycarbonate, polyurethanes, Teflon™, and derivatives thereof, etc.), GETEK (a blend of polypropylene oxide and fiberglass), etc.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

The substrates can be part of a larger device comprising a detection chamber that exposes a given volume of sample to the detection electrode. Generally, the detection chamber ranges from about 1 mL to 1 ml, with about 10 µL to 500 µL being preferred. As will be appreciated by those in the art, depending on the experimental conditions and assay, smaller or larger volumes may be used.

In some embodiments, the detection chamber and electrode are part of a cartridge that can be placed into a device comprising electronic components (an AC/DC voltage source, an ammeter, a processor, a read-out display, temperature controller, light source, etc.). In this embodiment, the interconnections from each electrode are positioned such that upon insertion of the cartridge into the device, connections between the electrodes and the electronic components are established.

Detection electrodes on circuit board material (or other substrates) are generally prepared in a wide variety of ways. In general, high purity gold is used, and it may be deposited on a surface via vacuum deposition processes (sputtering and evaporation) or solution deposition (electroplating or electroless processes). When electroplating is done, the substrate must initially comprise a conductive material; fiberglass circuit boards are frequently provided with copper foil. Frequently, depending on the substrate, an adhesion layer between the substrate and the gold in order to insure good mechanical stability is used. Thus, preferred embodiments utilize a deposition layer of an adhesion metal such as chromium, titanium, titanium/tungsten, tantalum, nickel or palladium, which can be deposited as above for the gold. When electroplated metal (either the adhesion metal or the electrode metal) is used, grain refining additives, frequently referred to in the trade as brighteners, can optionally be added to alter surface deposition properties. Preferred brighteners are mixtures of organic and inorganic species, with cobalt and nickel being preferred.

In general, the adhesion layer is from about 100 Å thick to about 25 microns (1000 microinches). The If the adhesion metal is electrochemically active, the electrode metal must be coated at a thickness that prevents "bleed-through"; if the adhesion metal is not electrochemically active, the electrode metal may be thinner. Generally, the electrode metal (preferably gold) is deposited at thicknesses ranging from about 500 Å to about 5 microns (200 microinches), with from about 30 microinches to about 50 microinches being preferred. In general, the gold is deposited to make electrodes ranging in size from about 5 microns to about 5 mm in diameter, with about 100 to 250 microns being preferred. The detection electrodes thus formed are then preferably cleaned and SAMs added, as is discussed below.

Thus, the present invention provides methods of making a substrate comprising a plurality of gold electrodes. The methods first comprise coating an adhesion metal, such as nickel or palladium (optionally with brightener), onto the substrate. Electroplating is preferred. The electrode metal, preferably gold, is then coated (again, with electroplating preferred) onto the adhesion metal. Then the patterns of the device, comprising the electrodes and their associated interconnections are made using lithographic techniques, particularly photolithographic techniques as are known in the art, and wet chemical etching. Frequently, a non-conductive chemically resistive insulating material such as solder mask or plastic is laid down using these photolithographic techniques, leaving only the electrodes and a connection point to the leads exposed; the leads themselves are generally coated.

The methods continue with the addition of SAMs as are described below. In a preferred embodiment, drop deposition techniques are used to add the required chemistry, i.e. the monolayer forming species, one of which is preferably a capture ligand comprising species. Drop deposition techniques are well known for making "spot" arrays. This is done to add a different composition to each electrode, i.e. to make an array comprising different capture ligands. Alternatively, the SAM species may be identical for each electrode, and this may be accomplished using a drop deposition technique or the immersion of the entire substrate or a surface of the substrate into the solution.

Thus, in a preferred embodiment, the electrode comprises a monolayer, comprising electroconduit forming species (EFS). As outlined herein, the efficiency of target analyte binding (for example, oligonucleotide hybridization) may increase when the analyte is at a distance from the electrode. Similarly, non-specific binding of biomolecules, including the target analytes, to an electrode is generally reduced when a monolayer is present. Thus, a monolayer facilitates the maintenance of the analyte away from the electrode surface. In addition, a monolayer serves to keep charged species away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accesibility to the electrode.

By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer.

In general, the SAMs of the invention can be generated in a number of ways and comprise a number of different components, depending on the electrode surface and the system used. For "mechanism-1" embodiments, preferred embodiments utilize two monolayer forming species: a monolayer forming species (including insulators or conductive oligomers) and a conductive oligomer species comprising the capture binding ligand, although as will be appreciated by those in the art, additional monolayer forming species can be included as well. For "mechanism-2" systems, the composition of the SAM depends on the detection electrode surface. In general, two basic "mechanism-2" systems are described; detection electrodes comprising "smooth" surfaces, such as gold ball electrodes, and those comprising "rough" surfaces, such as those that are made using commercial processes on PC circuit boards. In general, without being bound by theory, it appears that monolayers made on imperfect surfaces, i.e. "rough" surfaces, spontaneously form monolayers containing enough electroconduits even in the absence of EFS, probably due to the fact that the formation of a uniform monolayer on a rough surface is difficult. "Smoother" surfaces, however, may require the inclusion of sufficient numbers of EFS to generate the electroconduits, as the uniform surfaces allow a more uniform monolayer to form. Again, without being bound by theory, the inclusion of species that disturb the uniformity of the monolayer, for example by including a rigid molecule in a background of more flexible ones, causes electroconduits. Thus "smooth" surfaces comprise monolayers comprising three components: an insulator species, a EFS, and a species comprising the capture ligand, although in some circumstances, for example when the capture ligand species is included at high density, the capture ligand species can serve as the EFS. "Smoothness" in this context is not measured physically but rather as a function of an increase in the measured signal when EFS are included. That is, the signal from a detection electrode coated with monolayer forming species is compared to a signal from a detection electrode coated with monolayer forming species including a EFS. An increase indicates that the surface is relatively smooth, since the inclusion of a EFS served to facilitate the access of the ETM to the electrode. It should also be noted that while the discussion herein is mainly directed to gold electrodes and thiol-containing monolayer forming species, other types of electrodes and monolayer-forming species can be used.

It should be noted that the "electroconduits" of mechanism-2 systems do not result in direct contact of sample components with the electrode surface; that is, the electroconduits are not large pores or holes that allow physical access to the electrode. Rather, without being bound by theory, it appears that the electroconduits allow certain types of ETMs, particularly hydrophobic ETMs, to penetrate sufficiently into the monolayer to allow detection. However, other types of redox active species, including some hydrophilic species, do not penentrate into the monolayer, even with electroconduits present. Thus, in general, redox active species that may be present in the sample do not give substantial signals as a result of the electroconduits. While the exact system will vary with the composition of the SAM and the choice of the ETM, in general, the test for a suitable SAM to reduce non-specific binding that also has sufficient electroconduits for E™ detection is to add either ferrocene or ferrocyanide to the SAM; the former should give a signal and the latter should not.

Accordingly, in mechanism-1 systems, the monolayer comprises a first species comprising a conductive oligomer comprising the capture binding ligand, as is more fully outlined below, and a second species comprising a monolayer forming species, including either or both insulators or conductive oligomers.

In a preferred embodiment, the monolayer comprises electroconduit-forming species. By "electroconduit-forming species" or "EFS" herein is meant a molecule that is capable of generating sufficient electroconduits in a monolayer, generally of insulators such as alkyl groups, to allow detection of ETMs at the surface. In general, EFS have one or more of the following qualities: they may be relatively rigid molecules, for example as compared to an alkyl chain; they may attach to the electrode surface with a geometry different from the other monolayer forming species (for example, alkyl chains attached to gold surfaces with thiol groups are thought to attach at roughly 45° angles, and phenyl-acetylene chains attached to gold via thiols are thought to go down at 90° angles); they may have a structure that sterically interferes or interrupts the formation of a tightly packed monolayer, for example through the inclusion of branching groups such as alkyl groups, or the inclusion of highly flexible species, such as polyethylene glycol units; or they may be capable of being activated to form electroconduits; for example, photoactivatible species that can be selectively removed from the surface upon photoactivation, leaving electroconduits.

Preferred EFS include conductive oligomers, as defined below, and phenyl-acetylene-polyethylene glycol species. However, in some embodiments, the EFS is not a conductive oligomer.

In a preferred embodiment, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transfering electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons.

In a preferred embodiment, the conductive oligomers have a conductivity, S, of from between about $10^{-6}$ to about $10^4$ $\Omega^{-1}cm^{-1}$, with from about $10^{-5}$ to about $10^3$ $\Omega^{-1}cm^{-1}$ being preferred, with these S values being calculated for molecules ranging from about 20 Å to about 200 Å. As described below, insulators have a conductivity S of about $10^{-7}$ $\Omega^{-1}cm^{-1}$ or lower, with less than about $10^{-8}$ $\Omega^{-1}cm^{-1}$ being preferred. See generally Gardner et al., Sensors and Actuators A 51 (1995) 57-66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during synthesis of the components of the system, ii) during the attachment of the conductive oligomer to an electrode, or iii) during detection assays. In addition, conductive oligomers that will promote the formation of self-assembled monolayers are preferred.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 1:

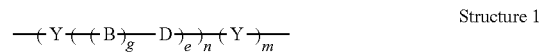

Structure 1

As will be understood by those in the art, all of the structures depicted herein may have additional atoms or structures; i.e. the conductive oligomer of Structure 1 may be attached to ETMs, such as electrodes, transition metal complexes, organic ETMs, and metallocenes, and to capture binding ligands, or to several of these. Unless otherwise noted, the conductive oligomers depicted herein will be attached at the left side to an electrode; that is, as depicted in Structure 1, the left "Y" is connected to the electrode as described herein. If the conductive oligomer is to be attached to a nucleic acid, the right "Y", if present, is attached to the nucleic acid, either directly or through the use of a linker, as is described herein.

In this embodiment, Y is an aromatic group, n is an integer from 1 to 50, g is either 1 or zero, e is an integer from zero to 10, and m is zero or 1. When g is 1, B-D is a bond able to conjugate with neighboring bonds (herein referred to as a "conjugated bond"), preferably selected from acetylene, B-D is a conjugated bond, preferably selected from acetylene, alkene, substituted alkene, amide, azo, —C═N— (including —N═C—, —CR═N— and —N═CR—), —Si═Si—, and —Si═C— (including —C═Si—, —Si═CR— and —CR═Si—). When g is zero, e is preferably 1, D is preferably carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO₂—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups.

The aromatic group may be substituted with a substitution group, generally depicted herein as R. R groups may be added as necessary to affect the packing of the conductive oligomers, i.e. R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first two or three oligomer subunits, depending on the average length of the molecules making up the monolayer.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—(CH$_2$)$_2$CH$_3$ and —O—(CH$_2$)$_4$CH$_3$ being preferred.

By "ester" herein is meant a —COOR group.

By "halogen" herein is meant bromine, iodine, chlorine, or fluorine. Preferred substituted alkyls are partially or fully halogenated alkyls such as CF$_3$, etc.

By "aldehyde" herein is meant —RCHO groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—CH$_2$)$_n$—, or with substitution groups) are also preferred.

Preferred substitution groups include, but are not limited to, methyl, ethyl, propyl, alkoxy groups such as —O—(CH$_2$)$_2$CH$_3$ and —O—(CH$_2$)$_4$CH$_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B-D is a bond linking two atoms or chemical moieties. In a preferred embodiment, B-D is a conjugated bond, containing overlapping or conjugated π-orbitals.

Preferred B-D bonds are selected from acetylene (—C≡C—, also called alkyne or ethyne), alkene (—CH=CH—, also called ethylene), substituted alkene (—CR=CR—, —CH=CR— and —CR=CH—), amide (—NH—CO— and —NR—CO— or —CO—NH— and —CO—NR—), azo (—N=N—), esters and thioesters (—CO—O—, —O—CO—, —CS—O— and —O—CS—) and other conjugated bonds such as (—CH=N—, —CR=N—, —N=CH— and —N=CR—), (—SiH=SiH—, —SiR=SiH—, —SiR=SiH—, and —SiR=SiR—), (—SiH=CH—, —SiR=CH—, —SiH=CR—, —SiR=CR—, —CH=SiH—, —CR=SiH—, —CH=SiR—, and —CR=SiR—). Particularly preferred B-D bonds are acetylene, alkene, amide, and substituted derivatives of these three, and azo. Especially preferred B-D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 1 conductive oligomer, e is preferably 1 and the D moiety may be carbonyl or a heteroatom moiety as defined above.

As above for the Y rings, within any single conductive oligomer, the B-D bonds (or D moieties, when g=0) may be all the same, or at least one may be different. For example, when m is zero, the terminal B-D bond may be an amide bond, and the rest of the B-D bonds may be acetylene bonds. Generally, when amide bonds are present, as few amide bonds as possible are preferable, but in some embodiments all the B-D bonds are amide bonds. Thus, as outlined above for the Y rings, one type of B-D bond may be present in the conductive oligomer within a monolayer as described below, and another type above the monolayer level, for example to give greater flexibility for nucleic acid hybridization when the nucleic acid is attached via a conductive oligomer.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient hybridization of nucleic acids on a surface, the hybridization should occur at a distance from the surface, i.e. the kinetics of hybridization increase as a function of the distance from the surface, particularly for long oligonucleotides of 200 to 300 basepairs. Accordingly, when a nucleic acid is attached via a conductive oligomer, as is more fully described below, the length of the conductive oligomer is such that the closest nucleotide of the nucleic acid is positioned from about 6 Å to about 100 Å (although distances of up to 500 Å may be used) from the electrode surface, with from about 15 Å to about 60 Å being preferred and from about 25 Å to about 60 Å also being preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B-D bond or D moiety, i.e. the D atom is attached to the nucleic acid either directly or via a linker. In some embodiments, for example when the conductive oligomer is attached to a phosphate of the ribose-phosphate backbone of a nucleic acid, there may be additional atoms, such as a linker, attached between the conductive oligomer and the nucleic acid. Additionally, as outlined below, the D atom may be the nitrogen atom of the amino-modified ribose. Alternatively, when m is 1, the conductive oligomer may terminate in Y, an aromatic group, i.e. the aromatic group is attached to the nucleic acid or linker.

As will be appreciated by those in the art, a large number of possible conductive oligomers may be utilized. These include conductive oligomers falling within the Structure 1 and Structure 8 formulas, as well as other conductive oligomers, as are generally known in the art, including for example, compounds comprising fused aromatic rings or Teflon®-like oligomers, such as —(CF$_2$)$_n$—, —(CHF)$_n$— and —(CFR)$_n$—. See for example, Schumm et al., Angew. Chem. Intl. Ed. Engl. 33:1361 (1994); Grosshenny et al., Platinum Metals Rev. 40(1):26-35 (1996); Tour, Chem. Rev. 96:537-553 (1996); Hsung et al., Organometallics 14:4808-4815 (1995; and references cited therein, all of which are expressly incorporated by reference.

Particularly preferred conductive oligomers of this embodiment are depicted below:

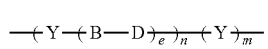

Structure 2

Structure 2 is Structure 1 when g is 1. Preferred embodiments of Structure 2 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B-D is acetylene and Y is phenyl or substituted phenyl (see Structure 4 below). A preferred embodiment of Structure 2 is also when e is one, depicted as Structure 3 below:

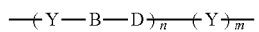

Structure 3

Preferred embodiments of Structure 3 are: Y is phenyl or substituted phenyl and B-D is azo; Y is phenyl or substituted phenyl and B-D is acetylene; Y is phenyl or substituted phenyl and B-D is alkene; Y is pyridine or substituted pyridine and B-D is acetylene; Y is thiophene or substituted thiophene and B-D is acetylene; Y is furan or substituted furan and B-D is acetylene; Y is thiophene or furan (or substituted thiophene or furan) and B-D are alternating alkene and acetylene bonds.

Most of the structures depicted herein utilize a Structure 3 conductive oligomer. However, any Structure 3 oligomers may be substituted with any of the other structures depicted herein, i.e. Structure 1 or 8 oligomer, or other conducting oligomer, and the use of such Structure 3 depiction is not meant to limit the scope of the invention.

Particularly preferred embodiments of Structure 3 include Structures 4, 5, 6 and 7, depicted below:

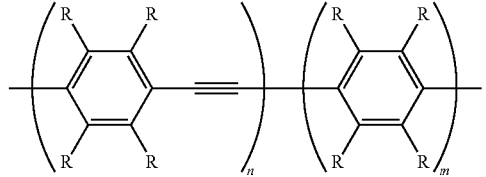

Structure 4

Particularly preferred embodiments of Structure 4 include: n is two, m is one, and R is hydrogen; n is three, m is zero, and R is hydrogen; and the use of R groups to increase solubility.

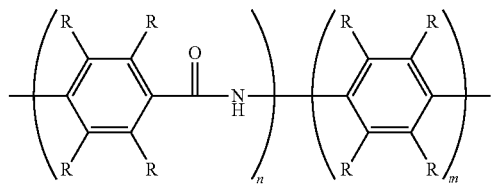

Structure 5

When the B-D bond is an amide bond, as in Structure 5, the conductive oligomers are pseudopeptide oligomers. Although the amide bond in Structure 5 is depicted with the carbonyl to the left, i.e. —CONH—, the reverse may also be used, i.e. —NHCO—. Particularly preferred embodiments of Structure 5 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

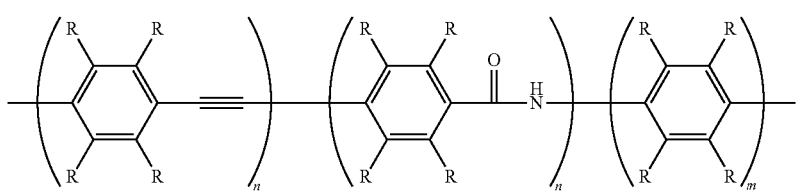

Structure 6

Preferred embodiments of Structure 6 include the first n is two, second n is one, m is zero, and all R groups are hydrogen, or the use of R groups to increase solubility.

Structure 7

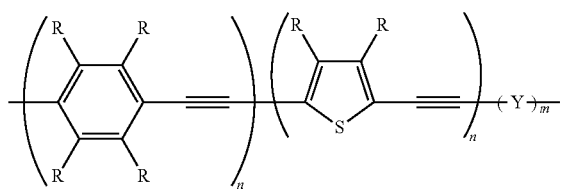

Preferred embodiments of Structure 7 include: the first n is three, the second n is from 1-3, with m being either 0 or 1, and the use of R groups to increase solubility.

In a preferred embodiment, the conductive oligomer has the structure depicted in Structure 8:

Structure 8

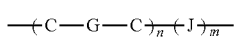

In this embodiment, C are carbon atoms, n is an integer from 1 to 50, m is 0 or 1, J is a heteroatom selected from the group consisting of oxygen, nitrogen, silicon, phosphorus, sulfur, carbonyl or sulfoxide, and G is a bond selected from alkane, alkene or acetylene, such that together with the two carbon atoms the C-G-C group is an alkene (—CH=CH—), substituted alkene (—CR=CR—) or mixtures thereof (—CH=CR— or —CR=CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma, bonds per conductive oligomer being preferred. Alkene bonds are preferred, and are generally depicted herein, although alkane and acetylene bonds may be substituted in any structure or embodiment described herein as will be appreciated by those in the art.

In some embodiments, for example when ETMs are not present, if m=0 then at least one of the G bonds is not an alkane bond.

In a preferred embodiment, the m of Structure 8 is zero. In a particularly preferred embodiment, m is zero and G is an alkene bond, as is depicted in Structure 9:

Structure 9

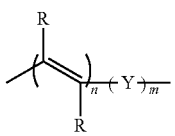

The alkene oligomer of structure 9, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 1 and 8.

In addition, the terminus of at least some of the conductive oligomers in the monolayer are electronically exposed. By "electronically exposed" herein is meant that upon the placement of an ETM in close proximity to the terminus, and after initiation with the appropriate signal, a signal dependent on the presence of the ETM may be detected. The conductive oligomers may or may not have terminal groups. Thus, in a preferred embodiment, there is no additional terminal group, and the conductive oligomer terminates with one of the groups depicted in Structures 1 to 9; for example, a B-D bond such as an acetylene bond. Alternatively, in a preferred embodiment, a terminal group is added, sometimes depicted herein as "Q". A terminal group may be used for several reasons; for example, to contribute to the electronic availability of the conductive oligomer for detection of ETMs, or to alter the surface of the SAM for other reasons, for example to prevent non-specific binding. For example, there may be negatively charged groups on the terminus to form a negatively charged surface such that when the nucleic acid is DNA or RNA the nucleic acid is repelled or prevented from lying down on the surface, to facilitate hybridization. Preferred terminal groups include —NH$_2$, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

It will be appreciated that the monolayer may comprise different conductive oligomer species, although preferably the different species are chosen such that a reasonably uniform SAM can be formed. Thus, for example, when nucleic acids are covalently attached to the electrode using conductive oligomers, it is possible to have one type of conductive oligomer used to attach the nucleic acid, and another type functioning to detect the ETM. Similarly, it may be desirable to have mixtures of different lengths of conductive oligomers in the monolayer, to help reduce non-specific signals. Thus, for example, preferred embodiments utilize conductive oligomers that terminate below the surface of the rest of the monolayer, i.e. below the insulator layer, if used, or below some fraction of the other conductive oligomers. Similarly, the use of different conductive oligomers may be done to facilitate monolayer formation, or to make monolayers with altered properties.

In a preferred embodiment, the monolayer forming species are "interrupted" conductive oligomers, containing an alkyl portion in the middle of the conductive oligomer.

In a preferred embodiment, the monolayer comprises photoactivatable species as EFS. Photoactivatable species are known in the art, and include 4,5-dimethoxy-2-nitrobenzyl ester, which can be photolyzed at 365 nm for 2 hours.

In a preferred embodiment, the monolayer may further comprise insulator moieties. By "insulator" herein is meant a substantially nonconducting oligomer, preferably linear. By "substantially nonconducting" herein is meant that the insulator will not transfer electrons at 100 Hz. The rate of electron transfer through the insulator is preferably slower than the rate through the conductive oligomers described herein.

In a preferred embodiment, the insulators have a conductivity, S, of about $10^{-7}$ $\Omega^{-1}$cm$^{-1}$ or lower, with less than about $10^{-8}$ $\Omega^{-1}$cm$^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

Suitable insulators are known in the art, and include, but are not limited to, —(CH$_2$)$_n$—, —(CRH)$_n$—, and —(CR$_2$)$_n$—, ethylene glycol or derivatives using other heteroatoms in place of oxygen, i.e. nitrogen or sulfur (sulfur derivatives are not preferred when the electrode is gold).

As for the conductive oligomers, the insulators may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. Similarly, the insulators may contain terminal groups, as outlined above, particularly to influence the surface of the monolayer.

The length of the species making up the monolayer will vary as needed. As outlined above, it appears that hybridization is more efficient at a distance from the surface. The species to which nucleic acids are attached (as outlined below, these can be either insulators or conductive oligomers) may be basically the same length as the monolayer forming species or longer than them, resulting in the nucleic acids being more accessible to the solvent for hybridization. In some embodiments, the conductive oligomers to which the nucleic acids are attached may be shorter than the monolayer.

As will be appreciated by those in the art, the actual combinations and ratios of the different species making up the monolayer can vary widely, and will depend on whether mechanism-1 or -2 is used. Generally, three component systems are preferred for mechanism-2 systems, with the first species comprising a capture probe containing species, attached to the electrode via either an insulator or a conductive oligomer. The second species are EFS, preferably conductive oligomers, and the third species are insulators. In this embodiment, the first species can comprise from about 90% to about 1%, with from about 20% to about 40% being preferred. For nucleic acids, from about 30% to about 40% is especially preferred for short oligonucleotide targets and from about 10% to about 20% is preferred for longer targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. To achieve these approximate proportions, preferred ratios of first:second:third species in SAM formation solvents are 2:2:1 for short targets, 1:3:1 for longer targets, with total thiol concentration (when used to attach these species, as is more fully outlined below) in the 500 µM to 1 mM range, and 833 µM being preferred.

Alternatively, two component systems can be used. In one embodiment, for use in either mechanism-1 or mechanism-2 systems, the two components are the first and second species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred. Alternatively, for mechanism-1 systems, the two components are the first and the third species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred.

In a preferred embodiment, the deposition of the SAM is done using aqueous solvents. As is generally described in Steel et al., Anal. Chem. 70:4670 (1998), Herne et al., J. Am. Chem. Soc. 119:8916 (1997), and Finklea, Electrochemistry of Organized Monolayers of Thiols and Related Molecules on Electrodes, from A. J. Bard, *Electroanalytical Chemistry: A Series of Advances*, Vol. 20, Dekker N.Y. 1966-, all of which are expressly incorporated by reference, the deposition of the SAM-forming species can be done out of aqueous solutions, frequently comprising salt.

The covalent attachment of the conductive oligomers and insulators may be accomplished in a variety of ways, depending on the electrode and the composition of the insulators and conductive oligomers used. In a preferred embodiment, the attachment linkers with covalently attached capture binding ligands (e.g. nucleosides or nucleic acids) as depicted herein are covalently attached to an electrode. Thus, one end or terminus of the attachment linker is attached to the nucleoside or nucleic acid, and the other is attached to an electrode. In some embodiments it may be desirable to have the attachment linker attached at a position other than a terminus, or even to have a branched attachment linker that is attached to an electrode at one terminus and to two or more nucleosides at other termini, although this is not preferred. Similarly, the attachment linker may be attached at two sites to the electrode, as is generally depicted in Structures 11-13. Generally, some type of linker is used, as depicted below as "A" in Structure 10, where "X" is the conductive oligomer, "I" is an insulator and the hatched surface is the electrode:

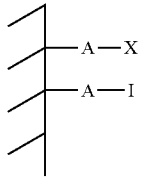

Structure 10

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al. Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the insulators and conductive oligomers may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 11, 12 and 13. As will be appreciated by those in the art, other such structures can be made. In Structures 11, 12 and 13, the A moiety is just a sulfur atom, but substituted sulfur moieties may also be used.

It should also be noted that similar to Structure 13, it may be possible to have a a conductive oligomer terminating in a single carbon atom with three sulfur moities attached to the electrode. Additionally, although not always depicted herein, the conductive oligomers and insulators may also comprise a "Q" terminal group.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 14, using the Structure 3 conductive oligomer, although as for all the structures depicted herein, any of the conductive oligomers, or combinations of conductive oligomers, may be used. Similarly, any of the conductive oligomers or insulators may also comprise terminal groups as described herein. Structure 14 depicts the "A" linker as comprising just a sulfur atom, although additional atoms may be present (i.e. linkers from the sulfur to the conductive oligomer or substitution groups). In addition, Structure 14 shows the sulfur atom attached to the Y aromatic group, but as will be appreciated by those in the art, it may be attached to the B-D group (i.e. an acetylene) as well.

Structure 14

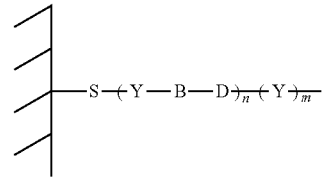

In a preferred embodiment, the electrode is a carbon electrode, i.e. a glassy carbon electrode, and attachment is via a nitrogen of an amine group. A representative structure is depicted in Structure 15. Again, additional atoms may be present, i.e. Z type linkers and/or terminal groups.

Structure 11

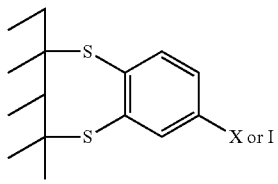

Structure 15

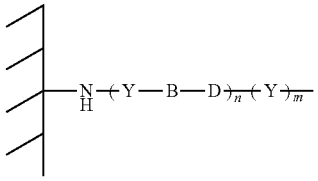

Structure 12

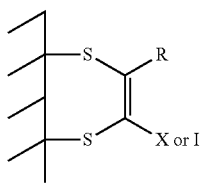

Structure 16

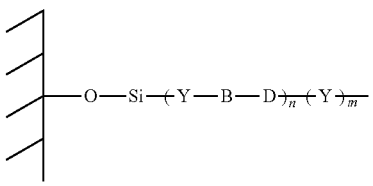

Structure 13

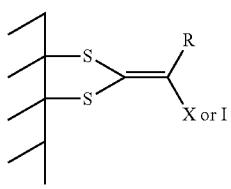

In Structure 16, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

The SAMs of the invention can be made in a variety of ways, including deposition out of organic solutions and deposition out of aqueous solutions. The methods outlined herein use a gold electrode as the example, although as will be appreciated by those in the art, other metals and methods may be used as well. In one preferred embodiment, indium-tin-oxide (ITO) is used as the electrode.

In a preferred embodiment, a gold surface is first cleaned. A variety of cleaning procedures may be employed, including, but not limited to, chemical cleaning or etchants (including Piranha solution (hydrogen peroxide/sulfuric acid) or aqua regia (hydrochloric acid/nitric acid), electrochemical methods, flame treatment, plasma treatment or combinations thereof.

Following cleaning, the gold substrate is exposed to the SAM species. When the electrode is ITO, the SAM species are phosphonate-containing species. This can also be done in a variety of ways, including, but not limited to, solution deposition, gas phase deposition, microcontact printing, spray deposition, deposition using neat components, etc. A preferred embodiment utilizes a deposition solution comprising a mixture of various SAM species in solution, generally thiol-containing species. Mixed monolayers that contain nucleic acids are usually prepared using a two step procedure. The thiolated nucleic acid is deposited during the first deposition step (generally in the presence of at least one other monolayer-forming species) and the mixed monolayer formation is completed during the second step in which a second thiol solution minus nucleic acid is added. The second step frequently involves mild heating to promote monolayer reorganization.

In a preferred embodiment, the deposition solution is an organic deposition solution. In this embodiment, a clean gold surface is placed into a clean vial. A binding ligand deposition solution in organic solvent is prepared in which the total thiol concentration is between micromolar to saturation; preferred ranges include from about 1 µM to 10 mM, with from about 400 uM to about 1.0 mM being especially preferred. In a preferred embodiment, the deposition solution contains thiol modified DNA (i.e. nucleic acid attached to an attachment linker) and thiol diluent molecules (either conductive oligomers or insulators, with the latter being preferred). The ratio of nucleic acid to diluent (if present) is usually between 1000:1 to 1:1000, with from about 10:1 to about 1:10 being preferred and 1:1 being especially preferred. The preferred solvents are tetrahydrofuran (THF), acetonitrile, dimethylforamide (DMF), ethanol, or mixtures thereof; generally any solvent of sufficient polarity to dissolve the capture ligand can be used, as long as the solvent is devoid of functional groups that will react with the surface. Sufficient nucleic acid deposition solution is added to the vial so as to completely cover the electrode surface. The gold substrate is allowed to incubate at ambient temperature or slightly above ambient temperature for a period of time ranging from seconds to hours, with 5-30 minutes being preferred. After the initial incubation, the deposition solution is removed and a solution of diluent molecule only (from about 1 µM to 10 mM, with from about 100 uM to about 1.0 mM being preferred) in organic solvent is added. The gold substrate is allowed to incubate at room temperature or above room temperature for a period of time (seconds to days, with from about 10 minutes to about 24 hours being preferred). The gold sample is removed from the solution, rinsed in clean solvent and used.

In a preferred embodiment, an aqueous deposition solution is used. As above, a clean gold surface is placed into a clean vial. A nucleic acid deposition solution in water is prepared in which the total thiol concentration is between about 1 uM and 10 mM, with from about 1 µM to about 200 uM being preferred. The aqueous solution frequently has salt present (up to saturation, with approximately 1M being preferred), however pure water can be used. The deposition solution contains thiol modified nucleic acid and often a thiol diluent molecule. The ratio of nucleic acid to diluent is usually between between 1000:1 to 1:1000, with from about 10:1 to about 1:10 being preferred and 1:1 being especially preferred. The nucleic acid deposition solution is added to the vial in such a volume so as to completely cover the electrode surface. The gold substrate is allowed to incubate at ambient temperature or slightly above ambient temperature for 1-30 minutes with 5 minutes usually being sufficient. After the initial incubation, the deposition solution is removed and a solution of diluent molecule only (10 uM-1.0 mM) in either water or organic solvent is added. The gold substrate is allowed to incubate at room temperature or above room temperature until a complete monolayer is formed (10 minutes-24 hours). The gold sample is removed from the solution, rinsed in clean solvent and used.

In a preferred embodiment, as outlined herein, a circuit board is used as the substrate for the gold electrodes. Formation of the SAMs on the gold surface is generally done by first cleaning the boards, for example in a 10% sulfuric acid solution for 30 seconds, detergent solutions, aqua regia, plasma, etc., as outlined herein. Following the sulfuric acid treatment, the boards are washed, for example via immersion in two Milli-Q water baths for 1 minute each. The boards are then dried, for example under a stream of nitrogen. Spotting of the deposition solution onto the boards is done using any number of known spotting systems, generally by placing the boards on an X-Y table, preferably in a humidity chamber. The size of the spotting drop will vary with the size of the electrodes on the boards and the equipment used for delivery of the solution; for example, for 250 µM size electrodes, a 30 nanoliter drop is used. The volume should be sufficient to cover the electrode surface completely. The drop is incubated at room temperature for a period of time (sec to overnight, with 5 minutes preferred) and then the drop is removed by rinsing in a Milli-Q water bath. The boards are then preferably treated with a second deposition solution, generally comprising insulator in organic solvent, preferably acetonitrile, by immersion in a 45° C. bath. After 30 minutes, the boards are removed and immersed in an acetonitrile bath for 30 seconds followed by a milli-Q water bath for 30 seconds. The boards are dried under a stream of nitrogen.

In a preferred embodiment, the electrode comprising the monolayer further comprises a capture binding ligand covalently attached to the electrode. This attachment can be via an attachment linker, which may be a conductive oligomer or an insulator. By "capture binding ligand" or "capture binding species" or "capture probe" herein is meant a compound that is used to probe for the presence of the target analyte, that will bind to the target analyte. ("Capture probe" or "anchor probe" are particularly used when the capture binding ligand is a nucleic acid). Generally, the capture binding ligand allows the attachment of a target analyte to the electrode, for the purposes of detection. As is more fully outlined below, attachment of the target analyte to the capture probe may be direct (i.e. the target analyte binds to the capture binding ligand) or indirect (one or more capture extender ligands are used). By "covalently attached" herein is meant that two moieties are attached by at least one bond, including sigma bonds, pi bonds and coordination bonds.

In a preferred embodiment, the binding is specific, and the binding ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding. In some embodiments, for example in the detection of certain biomolecules, the binding constants of the analyte to the binding ligand will be at least about $10^4$-$10^6$ $M^{-1}$, with at least about $10^5$ to $10^9 M^{-1}$ being preferred and at least about $10^7$-$10^9$ $M^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand may be a complementary nucleic acid. Similarly, the analyte may be a nucleic acid binding protein and the capture binding ligand is either single-stranded or double stranded nucleic acid; alternatively, the binding ligand may be a nucleic acid-binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates and inhibitors. As will be appreciated by those in the art, any two molecules that will associate may be used, either as an analyte or as the binding ligand. Suitable analyte/binding ligand pairs include, but are not limited to, antibodies/antigens, receptors/ligands, proteins/nucleic acid, enzymes/substrates and/or inhibitors, carbohydrates (including glycoproteins and glycolipids)/lectins, proteins/proteins, proteins/small molecules; and carbohydrates and their binding partners are also suitable analyte-binding ligand pairs. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT 4 receptor), transferrin receptor, epidermal growth factor receptor, low density lipoprotein receptor, high density lipoprotein receptor, epidermal growth factor receptor, leptin receptor, interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor, PDGF receptor, EPO receptor, TPO receptor, ciliary neurotrophic factor receptor, prolactin receptor, and T-cell receptors.

The method of attachment of the capture binding ligand to the attachment linker will generally be done as is known in the art, and will depend on the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups and thiol groups. These functional groups can then be attached, either directly or through the use of a linker, sometimes depicted herein as "Z". Linkers are known in the art; for example, homo- or hetero-bifunctional linkers are as well known (see 1994 Pierce Chemical Company catalog, technical section on cross-linkers, pages 155-200, incorporated herein by reference). Preferred Z linkers include, but are not limited to alkyl groups (including substituted alkyl groups and alkyl groups containing heteroatom moieties), with short alkyl groups, esters, amide, amine, epoxy groups and ethylene glycol and derivatives being preferred. Z may also be a sulfone group, forming sulfonamide.

In this way, capture binding ligands comprising proteins, lectins, nucleic acids, small organic molecules, carbohydrates, etc. can be added.

In a preferred embodiment, the capture binding ligand is attached directly to the electrode as outlined herein, for example via an attachment linker. Alternatively, the capture binding ligand may utilize a capture extender component. In this embodiment, the capture binding ligand comprises a first portion that will bind the target analyte and a second portion that can be used for attachment to the surface. FIG. 2C depicts the use of a nucleic acid component for binding to the surface, although this can be other binding partners as well.

A preferred embodiment utilizes proteinaceous capture binding ligands. As is known in the art, any number of techniques may be used to attach a proteinaceous capture binding ligand. "Protein" in this context includes proteins, polypeptides and peptides. A wide variety of techniques are known to add moieties to proteins. One preferred method is outlined in U.S. Pat. No. 5,620,850, hereby incorporated by reference in its entirety. The attachment of proteins to electrodes is known; see also Heller, Acc. Chem. Res. 23:128 (1990), and related work.

A preferred embodiment utilizes nucleic acids as the capture binding ligand, for example for when the target analyte is a nucleic acid or a nucleic acid binding protein, or when the nucleic acid serves as an aptamer for binding a protein; see U.S. Pat. Nos. 5,270,163, 5,475,096, 5,567,588, 5,595,877, 5,637,459, 5,683,867, 5,705,337, and related patents, hereby incorporated by reference. In this embodiment, the nucleic acid capture binding ligand is covalently attached to the electrode, via an "attachment linker", that can be either a conductive oligomer or via an insulator. Thus, one end of the attachment linker is attached to a nucleic acid, and the other end (although as will be appreciated by those in the art, it need not be the exact terminus for either) is attached to the electrode.

As is more fully outlined below, attachment of the target sequence to the capture probe may be direct (i.e. the target sequence hybridizes to the capture probe) or indirect (one or more capture extender probes are used). In addition, as is more fully outlined below, the capture probes may have both nucleic and non-nucleic acid portions. Thus, for example, flexible linkers such as alkyl groups, including polyethylene glycol linkers, may be used to get the nucleic acid portion of the capture probe off the electrode surface. This may be particularly useful when the target sequences are large, for example when genomic DNA or rRNA is the target.

The capture probe nucleic acid is covalently attached to the electrode, via an "attachment linker", that can be either a conductive oligomer or via an insulator. Thus, one end of the attachment linker is attached to a nucleic acid, and the other end (although as will be appreciated by those in the art, it need not be the exact terminus for either) is attached to the electrode. Thus, any of structures depicted herein may further comprise a nucleic acid effectively as a terminal group. Thus, the present invention provides compositions comprising nucleic acids covalently attached to electrodes as is generally depicted below in Structure 17:

Structure 17

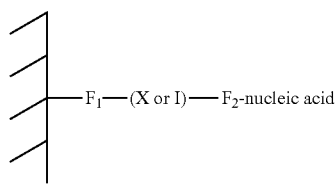

Structure 18

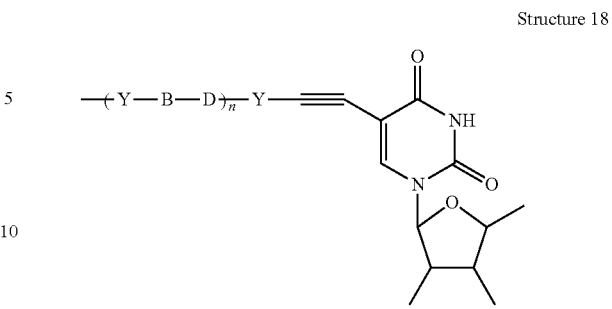

In Structure 17, the hatched marks on the left represent an electrode. X is a conductive oligomer and I is an insulator as defined herein. $F_1$ is a linkage that allows the covalent attachment of the electrode and the conductive oligomer or insulator, including bonds, atoms or linkers such as is described herein, for example as "A", defined below. $F_2$ is a linkage that allows the covalent attachment of the conductive oligomer or insulator to the nucleic acid, and may be a bond, an atom or a linkage as is herein described. $F_2$ may be part of the conductive oligomer, part of the insulator, part of the nucleic acid, or exogeneous to both, for example, as defined herein for "Z".

In a preferred embodiment, the capture probe nucleic acid is covalently attached to the electrode via a conductive oligomer. The covalent attachment of the nucleic acid and the conductive oligomer may be accomplished in several ways. In a preferred embodiment, the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occurring nucleic acids, although as will be appreciated by those in the art, similar techniques may be used with nucleic acid analogs.

In a preferred embodiment, the conductive oligomer is attached to the base of a nucleoside of the nucleic acid. This may be done in several ways, depending on the oligomer, as is described below. In one embodiment, the oligomer is attached to a terminal nucleoside, i.e. either the 3' or 5' nucleoside of the nucleic acid. Alternatively, the conductive oligomer is attached to an internal nucleoside.

The point of attachment to the base will vary with the base. Generally, attachment at any position is possible. In some embodiments, for example when the probe containing the ETMs may be used for hybridization, it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In one embodiment, the attachment is direct; that is, there are no intervening atoms between the conductive oligomer and the base. In this embodiment, for example, conductive oligomers with terminal acetylene bonds are attached directly to the base. Structure 18 is an example of this linkage, using a Structure 3 conductive oligomer and uridine as the base, although other bases and conductive oligomers can be used as will be appreciated by those in the art:

It should be noted that the pentose structures depicted herein may have hydrogen, hydroxy, phosphates or other groups such as amino groups attached. In addition, the pentose and nucleoside structures depicted herein are depicted non-conventionally, as mirror images of the normal rendering. In addition, the pentose and nucleoside structures may also contain additional groups, such as protecting, groups, at any position, for example as needed during synthesis.

In addition, the base may contain additional modifications as needed, i.e. the carbonyl or amine groups may be altered or protected, for example as is depicted in FIG. 18A of PCT US97/20014. This may be required to prevent significant dimerization of conductive oligomers instead of coupling to the iodinating base. In addition, changing the components of the palladium reaction may be desirable also. R groups may be preferred on longer conductive oligomers to increase solubility.

In an alternative embodiment, the attachment is any number of different Z linkers, including amide and amine linkages, as is generally depicted in Structure 19 using uridine as the base and a Structure 3 oligomer:

Structure 19:

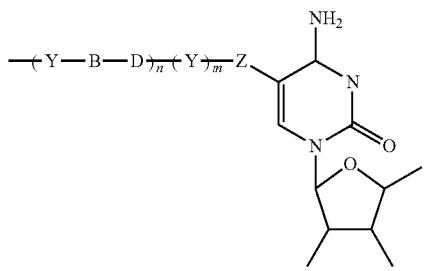

In this embodiment, Z is a linker. Preferably, Z is a short linker of about 1 to about 10 atoms, with from 1 to 5 atoms being preferred; that may or may not contain alkene, alkynyl, amine, amide, azo, imine, etc., bonds. Linkers are known in the art; for example, homo- or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages as discussed below.

In a preferred embodiment, the attachment of the nucleic acid and the conductive oligomer is done via attachment to the backbone of the nucleic acid. This may be done in a number of ways, including attachment to a ribose of the ribose-phosphate backbone, or to the phosphate of the backbone, or other groups of analogous backbones.

As a preliminary matter, it should be understood that the site of attachment in this embodiment may be to a 3' or 5' terminal nucleotide, or to an internal nucleotide, as is more fully described below.

In a preferred embodiment, the conductive oligomer is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4):714 (1977); Verheyden et al., J. Orrg. Chem. 36(2):250 (1971); McGee et al., J. Org. Chem. 61:781-785 (1996); Mikhailopulo et al., Liebigs. Ann. Chem. 513-519 (1993); McGee et al., Nucleosides & Nucleotides 14(6):1329 (1995), all of which are incorporated by reference). These modified nucleosides are then used to add the conductive oligomers.

A preferred embodiment utilizes amino-modified nucleosides. These amino-modified riboses can then be used to form either amide or amine linkages to the conductive oligomers. In a preferred embodiment, the amino group is attached directly to the ribose, although as will be appreciated by those in the art, short linkers such as those described herein for "Z" may be present between the amino group and the ribose.

In a preferred embodiment, an amide linkage is used for attachment to the ribose. Preferably, if the conductive oligomer of Structures 1-3 is used, m is zero and thus the conductive oligomer terminates in the amide bond. In this embodiment, the nitrogen of the amino group of the amino-modified ribose is the "D" atom of the conductive oligomer. Thus, a preferred attachment of this embodiment is depicted in Structure 20 (using the Structure 3 conductive oligomer):

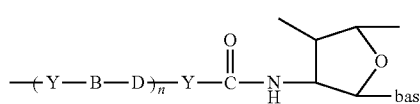

Structure 20

As will be appreciated by those in the art, Structure 20 has the terminal bond fixed as an amide bond.

In a preferred embodiment, a heteroatom linkage is used, i.e. oxo, amine, sulfur, etc. A preferred embodiment utilizes an amine linkage. Again, as outlined above for the amide linkages, for amine linkages, the nitrogen of the amino-modified ribose may be the "D" atom of the conductive oligomer when the Structure 3 conductive oligomer is used. Thus, for example, Structures 21 and 22 depict nucleosides with the Structures 3 and 9 conductive oligomers, respectively, using the nitrogen as the heteroatom, athough other heteroatoms can be used:

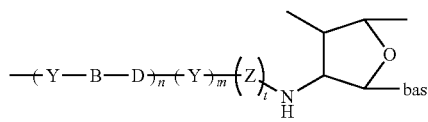

Structure 21

In Structure 21, preferably both m and t are not zero. A preferred Z here is a methylene group, or other aliphatic alkyl linkers. One, two or three carbons in this position are particularly useful for synthetic reasons; see PCT US97/20014.

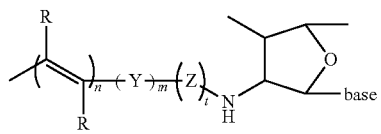

Structure 22

In Structure 22, Z is as defined above. Suitable linkers include methylene and ethylene.

In an alternative embodiment, the conductive oligomer is covalently attached to the nucleic acid via the phosphate of the ribose-phosphate backbone (or analog) of a nucleic acid. In this embodiment, the attachment is direct, utilizes a linker or via an amide bond. Structure 23 depicts a direct linkage, and Structure 24 depicts linkage via an amide bond (both utilize the Structure 3 conductive oligomer, although Structure 8 conductive oligomers are also possible). Structures 23 and 24 depict the conductive oligomer in the 3' position, although the 5' position is also possible. Furthermore, both Structures 23 and 24 depict naturally occurring phosphodiester bonds, although as those in the art will appreciate, non-standard analogs of phosphodiester bonds may also be used.

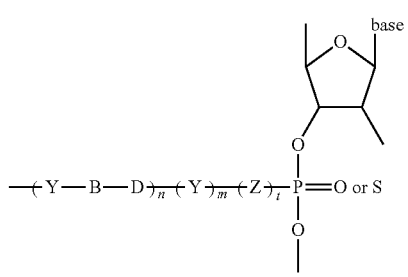

Structure 23

In Structure 23, if the terminal Y is present (i.e. m=1), then preferably Z is not present (i.e. t=0). If the terminal Y is not present, then Z is preferably present.

Structure 24 depicts a preferred embodiment, wherein the terminal B-D bond is an amide bond, the terminal Y is not present, and Z is a linker, as defined herein.

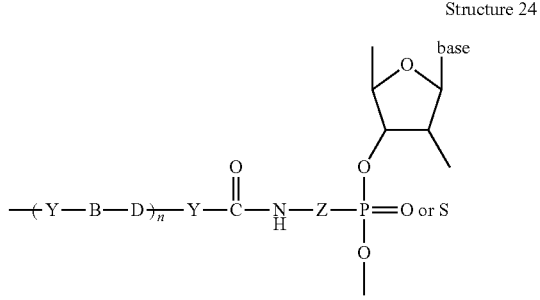

Structure 24

In a preferred embodiment, the conductive oligomer is covalently attached to the nucleic acid via a transition metal ligand. In this embodiment, the conductive oligomer is covalently attached to a ligand which provides one or more of the coordination atoms for a transition metal. In one embodiment, the ligand to which the conductive oligomer is attached also has the nucleic acid attached, as is generally depicted below in Structure 25. Alternatively, the conductive oligomer is attached to one ligand, and the nucleic acid is attached to another ligand, as is generally depicted below in Structure 26. Thus, in the presence of the transition metal, the conductive oligomer is covalently attached to the nucleic acid. Both of these structures depict Structure 3 conductive oligomers, although other oligomers may be utilized. Structures 25 and 26 depict two representative structures:

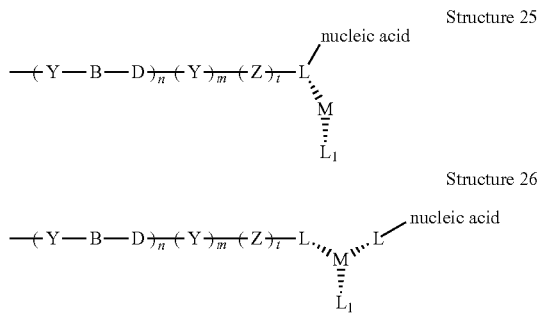

In the structures depicted herein, M is a metal atom, with transition metals being preferred. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinium, cobalt and iron.

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma ($\sigma$) donors) and organometallic ligands such as metallocene ligands (generally referred to in the literature as pi ($\pi$) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetraazacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with π-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (−1) ion, that yield a class of bis(cyclopentadieyl) metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene $[(C_5H_5)_2Fe]$ and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic π-bonded ligands such as the allyl(-1) ion, or butadiene yield potentially suitable organometallic compounds, and all such ligands, in conjuction with other π-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture. These combinations are depicted in representative structures using the conductive oligomer of Structure 3 are depicted in Structures 27 (using phenanthroline and amino as representative ligands), 28 (using ferrocene as the metal-ligand combination) and 29 (using cyclopentadienyl and amino as representative ligands).

Structure 27

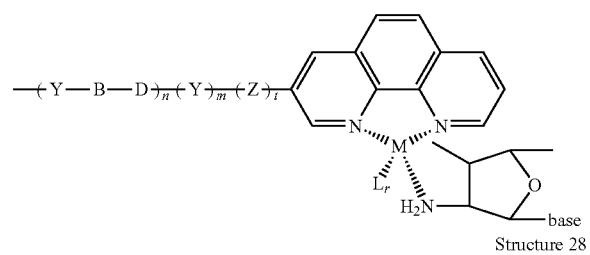

Structure 28

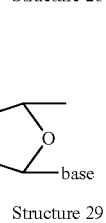

Structure 29

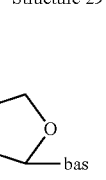

In addition to serving as attachments for conductive oligomers and electrodes, the above compositions can also be used as ETM labels. That is, as is outlined in FIGS. 19 and 20, transition metals (or other ETMs) attached to conductive oligomers can be added to the nucleic acids for detection. In this embodiment, without being bound by theory, the conductive oligomer, terminating preferably in an F1 linkage (a linkage that allows the attachment of the conductive oligomer to the surface), will penetrate the SAM and facilitate electron transfer between the ETM and the electrode. Without being bound by theory, this appears to allow rapid electron transfer, similar to a "mechanism-1" system, by providing a direct pathway for electrons; this is sometimes referred to herein as "hardwiring".

Surprisingly, the system appears to work whether or not the F1 moiety is protected; that is, a direct attachment may not be required to increase the frequency response of the ETM. Thus, the conductive oligomer can terminate either in an F1 moiety, an F1 moiety protected with a protecting group (see Greene, supra), or need not terminate in an F1 moiety at all; terminal groups such as are used on the surfaces of the SAMs may also be used. Alternatively, the bare terminus of the conductive oligomer may be sufficient.

In this embodiment, a plurality of ETMs per "branch" may be used. They may be attached as a group, e.g. as a metallocene polymer, terminating in the conductive oligomer, or may be substitution groups off of the conductive oligomer. In general, preferred embodiments utilize electronic conjugation between the ETMs and the conductive oligomer, to facilitate electron transfer.

In general, the length of the conductive oligomer in this embodiment will vary with the length of the SAM on the electrode, and preferred embodiments utilize two unit and three unit oligomers. Preferred conductive oligomers in this embodiment are the same as those outlined above for attachment of nucleic acids to electrodes, with phenyl-acetylene oligomers being the most preferred.

In this embodiment, the ETM with the attached conductive oligomer is generally synthesized, and then a phosphoramidite moiety is made.

In a preferred embodiment, the ligands used in the invention show altered fluoroscent properties depending on the redox state of the chelated metal ion. As described below, this thus serves as an additional mode of detection of electron transfer between the ETM and the electrode.

In a preferred embodiment, as is described more fully below, the ligand attached to the nucleic acid is an amino group attached to the 2' or 3' position of a ribose of the ribose-phosphate backbone. This ligand may contain a multiplicity of amino groups so as to form a polydentate ligand which binds the metal ion. Other preferred ligands include cyclopentadiene and phenanthroline.

The use of metal ions to connect the nucleic acids can serve as an internal control or calibration of the system, to evaluate the number of available nucleic acids on the surface. However, as will be appreciated by those in the art, if metal ions are used to connect the nucleic acids to the conductive oligomers, it is generally desirable to have this metal ion complex have a different redox potential than that of the ETMs used in the rest of the system, as described below. This is generally true so as to be able to distinguish the presence of the capture probe from the presence of the target sequence. This may be useful for identification, calibration and/or quantification. Thus, the amount of capture probe on an electrode may be compared to the amount of hybridized double stranded nucleic acid to quantify the amount of target sequence in a sample. This is quite significant to serve as an internal control of the sensor or system. This allows a measurement either prior to the addition of target or after, on the same molecules that will be used for detection, rather than rely on a similar but different control system. Thus, the actual molecules that will be used for the detection can be quantified prior to any experiment. This is a significant advantage over prior methods.

In a preferred embodiment, the capture probe nucleic acids are covalently attached to the electrode via an insulator. The attachment of nucleic acids to insulators such as alkyl groups is well known, and can be done to the base or the backbone, including the ribose or phosphate for backbones containing these moieties, or to alternate backbones for nucleic acid analogs.

In a preferred embodiment, there may be one or more different capture probe species on the surface. In some embodiments, there may be one type of capture probe, or one type of capture probe extender, as is more fully described below. Alternatively, different capture probes, or one capture probes with a multiplicity of different capture extender probes can be used. Similarly, it may be desirable to use auxiliary capture probes that comprise relatively short probe sequences, that can be used to "tack down" components of the system, for example the recruitment linkers, to increase the concentration of ETMs at the surface.

Thus the present invention provides electrodes, preferably comprising monolayers and capture binding ligands, useful in target analyte detection systems.

In a preferred embodiment, the assay complex comprises a first transport component comprising a first binding partner. The first transport component is used to transport the assay complex comprising the first component to the electrode, as is more described herein.

In a preferred embodiment, the first component is a particle. By "particle" or "microparticle" or "nanoparticle" or "bead" or "microsphere" herein is meant microparticulate matter. As will be appreciated by those in the art, the first particles can comprise a wide variety of materials, including, but not limited to, cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoria sol, carbon graphite, titanium dioxide, nylon, latex, and teflon may all be used. "*Microsphere Detection Guide*" from Bangs Laboratories, Fishers Ind. is a helpful guide. Preferred embodiments utilize magnetic particles and colloids.

The size of the particles will depend on their composition. The particles need not be spherical; irregular particles may be used. In addition, the particles may be porous, thus increasing the surface area of the particle available for attachment of binding ligands, capture moieties, or ETMs. In general, the size of the particles will vary with their composition; for example, magnetic particles are generally bigger than colloid particles. Thus, the particles have diameters ranging from 1-5 nm (colloids) to 200 μm (magnetic particles).

In a preferred embodiment, the first particle is a magnetic particle or a particle that can be induced to display magnetic properties. By "magnetic" herein is meant that the particle is attracted in a magnetic field, including ferromagnetic, paramagnetic, and diamagnetic. In this embodiment, the particles are preferably from about 0.001 to about 200 μm in diameter, with from about 0.05 to about 200 μm preferred, from about 0.1 to about 100 μm being particularly preferred, and from about 0.5 to about 10 μm being especially preferred.

In a preferred embodiment, the first particle is a colloid particle or nanoparticle. By "colloid" or "nanoparticle" herein is meant a particle that is small enough to stay suspended in solution in standard solvents and standard conditions. Generally, a colloid is a particle in the size range of 1 nm to 1 μm. A suspension of colloids is distinguishable from non-colloids in that their spatial distribution is largely unaltered by gravity during the time course of an experimental observation. As is known in the art, colloids can be made from a variety of materials; see Schmid, ed. Clusters and Colloids, VCH, Weinheim, 1994; Hayat ed. Colloidal Gold: Principles, Methods and Applications (Academic, San Diego, 1991); Bassell et al., J. Cell Biol. 126:863 1994; and Creighton et al., J. Chem. Soc. Faraday II 75:790 (1979), all of which are hereby incorporated by reference. Preferred colloids include, but are not limited to, those of Au, Se, Te, Co, Ni, Fe, Cu, Pt and other transition metals, and other colloids known in the art. It is known that many colloid particles are charged and thus naturally repel each other; for example, Au colloid particles are generally negatively charged. This facilitates non-aggregation except in the presence of target analyte as described below.

In some embodiments, the transport composition is not a particle, and is in solution. In this embodiment, the transport composition comprises a capture ligand as outlined below.

The first components comprise a first binding partner. By "binding partner" or "binding ligand" or grammatical equivalents herein is meant a compound that is used to probe for the presence of the target analyte, and that will bind to the target analyte. As for the capture binding ligands outlined herein, the composition of the binding ligand will depend on the composition of the target analyte, as generally described above.

Generally, the first binding ligands are attached to the transport component in a variety of ways, depending on whether the transport component is a particle, the composition of the particle, and the composition of the binding ligand.

In a preferred embodiment, the transport component is a particle, and attachment proceeds on the basis of the composition of the particle and the composition of the first binding ligand. In a preferred embodiment, depending on the composition of the particle, it will contain chemical functional groups for subsequent attachment of other moieties. For example, when the particle is a magnetic particle, magnetic particles with chemical functional groups such as amines are commercially available. Preferred functional groups for attachment are amino groups, carboxy groups, oxo groups and thiol groups, with amino groups being particularly preferred. Using these functional groups, the binding ligands can be attached using functional groups on the binding ligands. For example, proteins and nucleic acids containing amino groups can be attached to particles comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

When the transport particle is a colloid particle, attachment will again depend on the composition of the colloid and of the binding ligand, and generally proceeds as outlined above for attachment to electrodes.

The density of the binding ligand on the particle can vary widely, and will depend in part on the presence or absence of the other components on the particle, including, but not limited to, capture binding ligands, SAMs including conductive oligomers and insulators, charged moieties, etc. In general, when large target analytes are to be detected, such as large proteins or long nucleic acids, the density of the binding ligand is decreased, to allow sufficient "space" for the target analyte to bind.

In one embodiment, the transport component comprises a capture ligand that can be used for attachment to an electrode that comprises a capture binding partner. As defined herein for binding ligands, capture ligands and capture binding partners are pairs that specifically interact, such that the transport composition can be attached to the electrode. Capture ligands and capture binding partners may comprising a large number of different species, as is outlined above for binding ligands, with proteins and nucleic acids being particularly preferred. Thus, the capture ligand and capture binding partner can be used to transport the assay complex to the electrode surface, as is more fully described below.

In a preferred embodiment, the transport component is not a particle, and instead comprises a capture binding ligand and a first binding ligand. Again, the method of attachment will depend on the composition of each. In general, a variety of methods are known for the attachment of two proteins, including the use of linkers including polymers, and homo- and heterobifunctional linkers as described herein. In some cases, recombinant DNA technology can be utilized to make fusion proteins comprising at least a first domain comprising the first binding ligand and a second domain comprising the capture binding ligand. Similarly, when the binding ligand and capture binding ligand are both, nucleic acids, they may be generally contiguous sequences that are synthesized as such. Preferably in this embodiment, the reporter composition is a particle, preferably a gold colloid particle with a SAM including ETMs.

In a preferred embodiment, when the transport component does not comprise a particle, it is possible to use polymers, either linear or branched, that have a plurality of first binding ligands attached, using techniques known in the art. Upon binding of a plurality of target molecules and the reporter compositions, particularly when the reporter compositions comprise particles, it is possible to effect aggregation of the assay complex, leading to transport to the electrode surface. Thus, in this embodiment, there may or may not be capture binding ligands. Preferably in this embodiment, the reporter composition is a particle, preferably a gold colloid particle with a SAM including ETMs.

In a preferred embodiment, the transport particle further comprises a self-assembled monolayer (SAM), particularly when the transport particle is a gold colloid particle. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. The SAM may comprise attachment linkers, including conductive oligomers and insulators either together or each separately, and the composition of the SAM may depend on its location; that is, as is more fully described below, SAMs on the electrode must comprise at least some conductive oligomers. As outlined herein, the efficiency of oligonucleotide hybridization, and other binding events, may increase when the analyte is at a distance from the surface. Similarly, non-specific binding of biomolecules, including nucleic acids, to a surface is generally reduced when a monolayer is present. Thus, a monolayer facilitates the maintenance of the analyte away from the surface. In addition, when the SAM is on the electrode, a monolayer serves to keep charge carriers away from the surface of the electrode. Thus, this layer helps to prevent direct electrical contact between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accesibility to the electrode.

As will be appreciated by those in the art, the actual combinations and ratios of the different species making up the monolayer can vary widely, and will depend on where the monolayer is, i.e. on a transport particle, a reporter particle, or on the electrode. For attachment on a transport particle, generally two, three or four component systems are preferred. The components are as follows. The first species comprises a binding ligand containing species (that is generally attached to the surface via an attachment linker, i.e. either an insulator or a conductive oligomer; as is more fully described below). The second species are the conductive oligomers. The third species are insulators. The fourth species is a charged species that will prevent the particles of the invention from aggregating in the absence of the target analyte; this may or may not be required, depending on the particle and the binding ligand; that is, in some instances the binding ligand may comprise a charged species. For example, when the binding ligand is a nucleic acid, the nucleic acids provide the required charge and a fourth species is not required. The second, third and fourth species are optional on a transport particle, particularly a magnetic particle.

A representative three component system comprises the first, second and third species. In this embodiment, the actual ratio of the components will vary, in part depending on the size of the binding ligand and target analyte; i.e. for larger ligands or analytes, a lower amount of first species is desirable. Thus, a preferred embodiment utilizes a three component system with the first species comprising from about 90% to about 1%, with from about 20% to about 40% being preferred, and from about 30% to about 40% being especially preferred for small targets and from about 10% to about 20% preferred for larger targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. Preferred ratios of first:second:third species are 2:2:1 for small targets, 1:3:1 for larger targets, with total thiol concentration in the 500 µM to 1 mM range, and 833 µM being preferred.

In a preferred embodiment, two component systems are used, comprising the first and second species. In this embodiment, the first species can comprise from about 90% to about 1%, with from about 1% to about 40% being preferred, and from about 10% to about 40% being especially preferred. The second species can comprise from about 1% to about 90%, with from about 10% to about 60% being preferred, and from about 20% to about 40% being especially preferred.

In some embodiments, it is possible to avoid the use of a first transport component completely. What is important in this embodiment is that the reporter compositions are unable to associate with the electrode in the absence of target analyte. This can be done in two different ways. In one embodiment, two reporter particles are used; that is, when the aggregation of the particles is used to transport the assay complex to the electrode as is more fully outlined below, it is possible to use a first and a second reporter particle, each containing a binding ligand for a different portion of the target analyte and each containing ETMs, as is generally depicted in FIG. 1F. In this embodiment, the specificity of the system is achieved through the use of a reporter particles that will not settle in the absence of aggregation. That is, in the absence of target analyte, the two reporter particles stay suspended in solution; upon the introduction of the target analyte, large "cross-linked" aggregation assay complexes are formed that can settle or be brought into contact with the electrode. Alternatively, it is possible to use the target analyte as the transport component; that is, part of the target analyte is used as a capture ligand, as described above and depicted in FIGS. 1E and 2, with one or more reporter compositions.

Generally, the first transport component does not comprise any ETM labels to decrease the amount of background signal. However, it is possible to use transport components that do comprise ETMs; in this embodiment, it is important that the first transport component does not contain the same ETM labels that are used in the reporter components. For example, ETM labels with different redox potentials may be used, such that the ETM labels on the reporter components are distinguishable from the labels on the transport components. Alternatively, other types of labels, such as fluorescent labels, may be used on the components. This may find use in the development of controls and calibration of the system.

In addition to the first components, the compositions of the invention further comprise a reporter composition that is used to signal the presence of the target analyte.

In a preferred embodiment, the reporter composition comprises a second particle. As defined above, the second particle may comprise a large number of different compositions. However, if the transport mechanism used is magnetic attraction, it is preferred in this embodiment that the second particle is non-magnetic.

In a preferred embodiment, the second particle is a colloid particle as defined above. Particularly preferred are gold colloid particles, due to the ease of attachment of sulfur-containing moieties.

In a preferred embodiment, the reporter composition is not a particle. In this embodiment, the reporter composition comprises a second binding ligand and at least one ETM, as defined below and shown in FIGS. 3, 4 and 5. Generally in this embodiment the reporter composition comprises a recruitment linker that has attached ETMs.

The reporter composition comprises a second binding ligand, as outlined above. The second binding ligand can be the same or different from the first binding ligand. In addition, the compositions of the invention (including both the transport and the reporter compositions), may comprise multiple different binding ligands.

The reporter composition further comprises at least one, and preferably a plurality, of signalling moieties or labels that can be used to detect the reporter compositions or assay complexes containing them, particularly reporter particles including colloids. Suitable signalling moieties include any detectable labels, including, but not limited to, labels detectable optically, fluorescently, electronically, electrochemically, radioactively, labels detectable via chemiluminescence, electrochemiluminesce, enzymes, fluorescence-resonance energy transfer (FRET), and RAMAN techniques. Thus, signalling moieties include, but are not limited to, electron transfer moieties, fluorescent moieties, radioisotopic moieties, optical dyes, RAMAN labels, etc.

In a preferred embodiment, the signalling moieties are electron transfer moieties. The terms "electron donor moiety", "electron acceptor moiety", and "electron transfer moieties" (ETMs) or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred ETMs include, but are not limited to, transition metal complexes, organic ETMs, and electrodes.

In a preferred embodiment, the ETMs are transition metal complexes. Transition metals are those whose atoms have a partial or complete d shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinium, cobalt and iron.

The transition metals are complexed with a variety of ligands, L, to form suitable transition metal complexes, as is well known in the art. The ligands provide the coordination atoms for the binding of the metal ion. As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma ($\sigma$) donors) and organometallic ligands such as metallocene ligands (generally referred to in the literature as pi ($\pi$) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with $\delta$-bonded organic ligand with donor atoms as heterocyclic or exocyclic substituents, there is available a wide variety of transition metal organometallic compounds with π-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (−1) ion, that yield a class of bis(cyclopentadieyl) metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene $[(C_5H_5)_2Fe]$ and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions: Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic π-bonded ligands such as the allyl(−1) ion, or butadiene yield potentially suitable organometallic compounds, and all such ligands, in conjuction with other π-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture.

In addition to transition metal complexes, other organic electron donors and acceptors may be attached for use in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2,1,9-def:6,5,10-d'e'f')diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and subsitituted derivatives of these compounds.

In one embodiment, the electron donors and acceptors are redox proteins as are known in the art. However, redox proteins in many embodiments are not preferred.

The number of ETMs per reporter composition can vary, and can depend on the composition of the reporter composition (i.e. whether it is a particle) and the method of attachment, as is more fully described below. In a preferred embodiment, a plurality of ETMs are used. As is shown in the examples, the use of multiple ETMs provides signal amplification and thus allows more sensitive detection limits. Generally from one to millions or more can be used.

The ETMs may be attached to the reporter compositions in a variety of ways, including methods described in WO 98/20162 and U.S. Ser. No. 09/135,183, filed Aug. 17, 1998 (now abandoned), both of which are hereby incorporated by reference in their entirety. In a preferred embodiment, as is more fully outlined below, it is desirable to attach the ETMs to the reporter composition in a manner that may maximize "crosstalk" as between different ETMs; that is, to maximize the possible conjugation of the system. This generally involves using either closely packed ETMs, as is generally depicted in FIGS. 4 and 5, or, when using colloid particles, conductive oligomers to attach the ETMs to the colloid particle, as is generally depicted in FIG. 1. Without being bound by theory, it appears that the use of ETMs attached to the metallic colloid particle via conductive oligomers allows electron transfer between ETMs on the entire particle rather than just those in spatial proximity to the electrode; that is the system is conjugated, allowing "access" of most or all of the ETMs on a particular reporter composition.

Accordingly, in a preferred embodiment, the ETM is attached to the reporter composition in a variety of ways.

In a preferred embodiment, the ETM is attached directly to the reporter composition, i.e. directly to the particle. This may be done as is generally outlined above for the attachment of binding ligands to magnetic particles or other particles, using functional groups on both the particle and the ETMs for attachment.

In a preferred embodiment, the reporter composition is a particle, and the ETM is attached via an attachment linker. The method of attachment will depend on the composition of the ETM and the attachment linker as will be appreciated by those in the art. In a preferred embodiment, the reporter composition is a particle and the attachment linker is a conductive oligomer. Preferred methods of attachment for this embodiment when the binding ligand is a nucleic acid are outlined in WO 98/20162, hereby incorporated by reference in its entirety; see particularly structures 31-34.

In a preferred embodiment, the ETM is attached to the terminus of the attachment linker, as depicted below in Structures 17, 18, 19 and 20. These structures depict the preferred embodiment of conductive oligomers as the attachment linkers, although insulators are useful as well. In addition, these structures depict metallocenes as the ETMs, although as will be appreciated by those in the art, other ETMs may be used as well. These structures depict the use of a single ETM per attachment linker, although as will be appreciated by those in the art, "branched" attachment linkers may also be used to result in multiple ETMs at the termini of the linker; in addition, ETMs may be attached as substitution groups along the length of the linker as well. In this embodiment, the attachment linkers basically form a SAM.

Structure 17

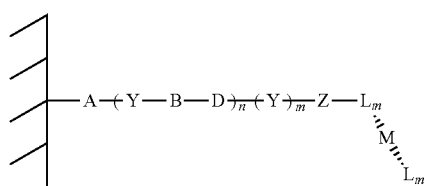

Structure 17 utilizes a Structure 10 conductive oligomer, although as will be appreciated by those in the art, other conductive oligomers may be used. Preferred embodiments of Structure 17 are depicted below.

Structure 18

Structure 19

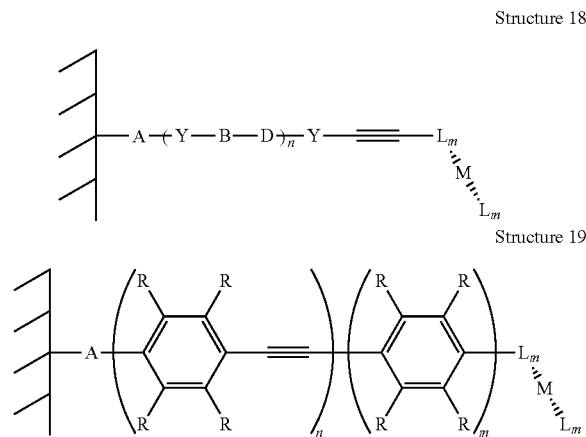

Preferred R groups of Structure 19 are hydrogen.

Structure 20

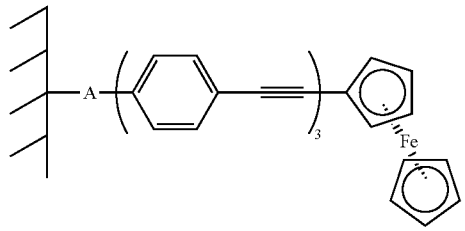

These compositions are synthesized as follows. The conductive oligomer linked to the metallocene is made as described herein; see also, Hsung et al., Organometallics 14:4808-4815 (1995); and Bumm et al., Science 271:1705 (1996), both of which are expressly incorporated herein by reference. The conductive oligomer is then attached to the electrode using the novel ethylpyridine protecting group, as outlined herein.

Alternatively, the ETMs can be attached as a plurality of ETMs as is generally outlined below for non-particle reporter compositions, using components as is generally outlined in FIG. 3.

In a preferred embodiment, the reporter composition is a particle and the attachment linker is an insulator. This is generally done using the above techniques as will be appreciated by those in the art. In a preferred embodiment, the reporter composition is not a particle and the binding ligand is linked either directly or indirectly to at least one ETM. This can be done directly, by attaching the binding ligand directly to the ETM, again generally by using chemical functionalities on each, as is generally described above. Similarly, linkers can be used, including polymers and homo- and heterobifunctional tinkers as described herein.

In a preferred embodiment, a recruitment linker comprising a plurality of ETMs is used, either for attachment to the binding ligand or for attachment to a particle comprising the binding ligand. This is particularly preferred when a particle is not used to allow more signal per target analyte, although as outlined above, these techniques can be used with particles as well. In this embodiment, the recruitment linker can be virtually any polymer, with nucleic acid being preferred, particularly when a particle is not used and the ETMs are to be linked directly to a nucleic acid binding ligand; this allows the synthesis of the reporter composition to be done in one step. In some embodiments, as is more fully outlined below, the recruitment linker may comprise double-stranded portions.

Thus, as will be appreciated by those in the art, there are a variety of configurations that can be used. In a preferred embodiment, the recruitment linker is nucleic acid (including analogs), and attachment of the ETMs can be via (1) a base; (2) the backbone, including the ribose, the phosphate, or comparable structures in nucleic acid analogs; (3) nucleoside replacement, described below; or (4) metallocene polymers, as described below. In a preferred embodiment, the recruitment linker is non-nucleic acid, and can be either a metallocene polymer or an alkyl-type polymer (including heteroalkyl, as is more fully described below) containing ETM substitution groups. These options are generally depicted in FIG. 3.

In a preferred embodiment, the recruitment linker is a nucleic acid, and comprises covalently attached ETMs. The ETMs may be attached to nucleosides within the nucleic acid in a variety of positions. Preferred embodiments include, but are not limited to, (1) attachment to the base of the nucleoside, (2) attachment of the ETM as a base replacement, (3) attachment to the backbone of the nucleic acid, including either to a ribose of the ribose-phosphate backbone or to a phosphate moiety, or to analogous structures in nucleic acid analogs, and (4) attachment via metallocene polymers, with the latter being preferred.

In a preferred embodiment, the ETM is attached to the base of a nucleoside as is generally outlined herein and in WO 98/20162 for the attachment of conductive oligomers. Attachment can be to an internal nucleoside or a terminal nucleoside, or combinations of these.

Ligands containing aromatic groups can be attached via acetylene linkages as is known in the art (see Comprehensive Organic Synthesis, Trost et al., Ed., Pergamon Press, Chapter 2.4: Coupling Reactions Between sp$^2$ and sp Carbon Centers, Sonogashira, pp 521-549, and pp 950-953, hereby incorporated by reference). Structure 21 depicts a representative structure in the presence of the metal ion and any other necessary ligands; Structure 21 depicts uridine, although as for all the structures herein, any other base may also be used.

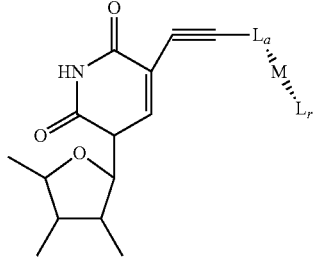

Structure 21

$L_a$ is a ligand, which may include nitrogen, oxygen, sulfur or phosphorus donating ligands or organometallic ligands such as metallocene ligands. Suitable $L_a$ ligands include, but not limited to, phenanthroline, imidazole, bpy and terpy. L, and M are as defined above. Again, it will be appreciated by those in the art, a linker ("Z") may be included between the nucleoside and the ETM.

Similarly, as for the conductive oligomers, the linkage may be done using a linker, which may utilize an amide linkage (see generally Telser et al., J. Am. Chem. Soc. 111:7221-7226 (1989); Telser et al., J. Am. Chem. Soc. 111:7226-7232 (1989), both of which are expressly incorporated by reference). These structures are generally depicted below in Structure 22, which again uses uridine as the base, although as above, the other bases may also be used:

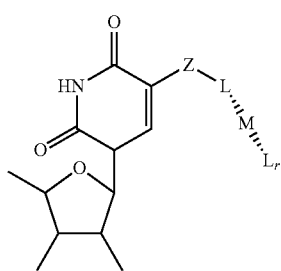

Structure 22

In this embodiment, L is a ligand as defined above, with $L_r$ and M as defined above as well. Preferably, L is amino, phen, byp and terpy.

In a preferred embodiment, the ETM attached to a nucleoside is a metallocene; i.e. the L and $L_r$ of Structure 22 are both metallocene ligands, $L_m$, as described above. Structure 23 depicts a preferred embodiment wherein the metallocene is ferrocene, and the base is uridine, although other bases may be used:

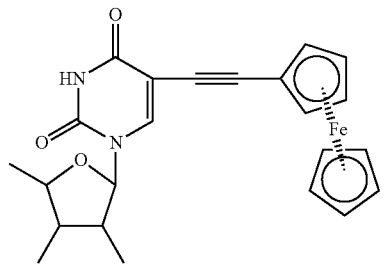

Structure 23

Preliminary data suggest that Structure 23 may cyclize, with the second acetylene carbon atom attacking the carbonyl oxygen, forming a furan-like structure. Preferred metallocenes include ferrocene, cobaltocene and osmiumocene.

In a preferred embodiment, the ETM is attached to a ribose at any position of the ribose-phosphate backbone of the nucleic acid, i.e. either the 5' or 3' terminus or any internal nucleoside. Ribose in this case can include ribose analogs. As is known in the art, nucleosides that are modified at either the 2' or 3' position of the ribose can be made, with nitrogen, oxygen, sulfur and phosphorus-containing modifications possible. Amino-modified and oxygen-modified ribose is preferred. See generally PCT publication WO 95/15971, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well, or a conductive oligomer between the ribose and the ETM. Preferred embodiments utilize attachment at the 2' or 3' position of the ribose, with the 2' position being preferred. Thus for example, conductive oligomers may be replaced by ETMs; alternatively, the ETMs may be added to the free terminus of the conductive oligomer.

In a preferred embodiment, a metallocene serves as the ETM, and is attached via an amide bond as depicted below in Structure 24. The examples outline the synthesis of a preferred compound when the metallocene is ferrocene.

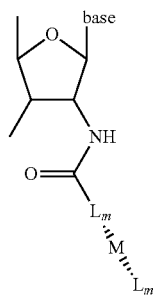

Structure 24

In a preferred embodiment, amine linkages are used, as is generally depicted in Structure 25.

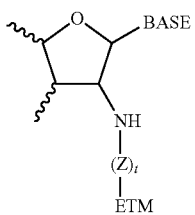

Structure 25

Z is a linker, as defined herein, with 1-16 atoms being preferred, and 2-4 atoms being particularly preferred, and t is either one or zero.

In a preferred embodiment, oxo linkages are used, as is generally depicted in Structure 26.

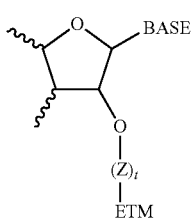

Structure 26

In Structure 26, Z is a linker, as defined herein, and t is either one or zero. Preferred Z linkers include alkyl groups including heteroalkyl groups such as $(CH_2)n$ and $(CH_2CH_2O)n$, with n from 1 to 10 being preferred, and n=1 to 4 being especially preferred, and n=4 being particularly preferred.

Linkages utilizing other heteroatoms are also possible.

In a preferred embodiment, an ETM is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid, where the heteroatom (i.e. nitrogen) serves as a transition metal ligand (see PCT publication WO 95/15971, incorporated by reference). Alternatively, the conductive oligomers depicted in the structures may be replaced by ETMs. In a preferred embodiment, the composition has the structure shown in Structure 25.

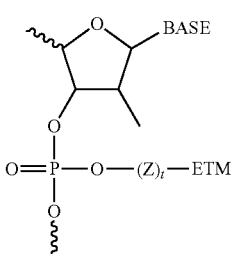

Structure 25

In Structure 25, the ETM is attached via a phosphate linkage, generally through the use of a linker, Z. Preferred Z linkers include alkyl groups, including heteroalkyl groups such as $(CH_2)_n$, $(CH_2CH_2O)_n$, with n from 1 to 10 being preferred, and n=1 to 4 being especially preferred, and n=4 being particularly preferred.

When the ETM is attached to the base or the backbone of the nucleoside, it is possible to attach the ETMs via "dendrimer" structures, as is more fully outlined below. As is generally depicted in the Figures, alkyl-based linkers can be used to create multiple branching structures comprising one or more ETMs at the terminus of each branch. Generally, this is done by creating branch points containing multiple hydroxy groups, which optionally can then be used to add additional branch points. The terminal hydroxy groups can then be used in phosphoramidite reactions to add ETMs, as is generally done below for the nucleoside replacement and metallocene polymer reactions.

In a preferred embodiment, an ETM such as a metallocene is used as a "nucleoside replacement", serving as an ETM. For example, the distance between the two cyclopentadiene rings of ferrocene is similar to the orthongonal distance between two bases in a double stranded nucleic acid. Other metallocenes in addition to ferrocene may be used, for example, air stable metallocenes such as those containing cobalt or ruthenium. Thus, metallocene moieties may be incorporated into the backbone of a nucleic acid, as is generally depicted in Structure 26 (nucleic acid with a ribose-phosphate backbone) and Structure 27 (peptide nucleic acid backbone). Structures 26 and 27 depict ferrocene, although as will be appreciated by those in the art, other metallocenes may be used as well. In general, air stable metallocenes are preferred, including metallocenes utilizing ruthenium and cobalt as the metal.

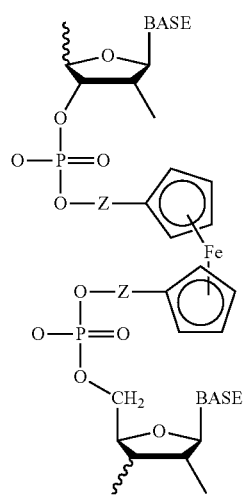

Structure 26

In Structure 26, Z is a linker as defined above, with generally short, alkyl groups, including heteroatoms such as oxygen being preferred. Generally, what is important is the length of the linker, such that minimal perturbations of a double stranded nucleic acid is effected, as is more fully described below. Thus, methylene, ethylene, ethylene glycols, propylene and butylene are all preferred, with ethylene and ethylene glycol being particularly preferred. In addition, each Z linker may be the same or different. Structure 26 depicts a ribose-phosphate backbone, although as will be appreciated by those in the art, nucleic acid analogs may also be used, including ribose analogs and phosphate bond analogs.

51

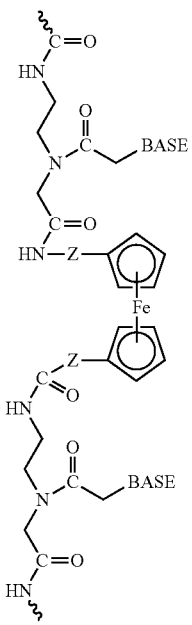

Structure 27

In Structure 27, preferred Z groups are as listed above, and again, each Z linker can be the same or different. As above, other nucleic acid analogs may be used as well.

In addition, although the structures and discussion above depicts metallocenes, and particularly ferrocene, this same general idea can be used to add ETMs in addition to metallocenes, as nucleoside replacements or in polymer embodiments, described below. Thus, for example, when the ETM is a transition metal complex other than a metallocene, comprising one, two or three (or more) ligands, the ligands can be functionalized as depicted for the ferrocene to allow the addition of phosphoramidite groups. Particularly preferred in this embodiment are complexes comprising at least two ring (for example, aryl and substituted aryl) ligands, where each of the ligands comprises functional groups for attachment via phosphoramidite chemistry. As will be appreciated by those in the art, this type of reaction; creating polymers of ETMs either as a portion of the backbone of the nucleic acid or as "side groups" of the nucleic acids, to allow amplification of the signals generated herein, can be done with virtually any ETM that can be functionalized to contain the correct chemical groups.

In addition, as is more fully outlined below, it is possible to incorporate more than one metallocene into the backbone, either with nucleotides in between and/or with adjacent metallocenes. When adjacent metallocenes are added to the backbone, this is similar to the process described below as "metallocene polymers"; that is, there are areas of metallocene polymers within the backbone.

In addition to the nucleic acid substitutent groups, it is also desirable in some instances to add additional substituent groups to one or both of the aromatic rings of the metallocene (or ETM). Substituent groups on an ETM, particularly metallocenes such as ferrocene, may be added to alter the redox properties of the ETM. Thus, for example, in some embodiments, it may be desirable to have different ETMs attached in different ways (i.e. base or ribose attachment), on different components, or for different purposes (for example, calibration or as an internal standard). Thus, the addition of substituent groups on the metallocene may allow two different ETMs to be distinguished.

52

In order to generate these metallocene-backbone nucleic acid analogs, the intermediate components are also provided. Thus, in a preferred embodiment, the invention provides phosphoramidite metallocenes, as generally depicted in Structure 28:

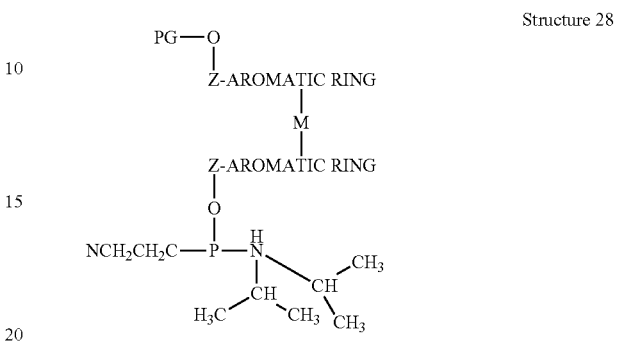

Structure 28

In Structure 28, PG is a protecting group, generally suitable for use in nucleic acid synthesis, with DMT, MMT and TMT all being preferred. The aromatic rings can either be the rings of the metallocene, or aromatic rings of ligands for transition metal complexes or other organic ETMs. The aromatic rings may be the same or different, and may be substituted as discussed herein. Structure 29 depicts the ferrocene derivative:

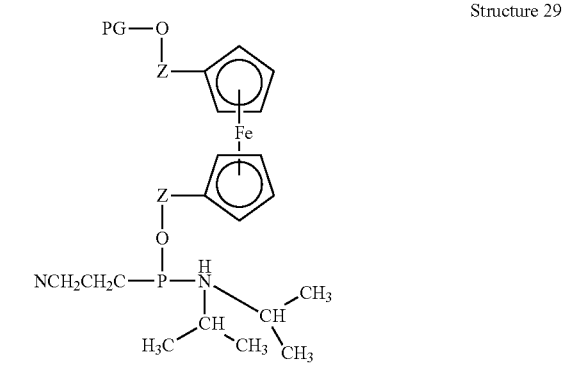

Structure 29

These phosphoramidite analogs can be added to standard oligonucleotide syntheses as is known in the art.

Structure 30 depicts the ferrocene peptide nucleic acid (PNA) monomer, that can be added to PNA synthesis as is known in the art and depicted within the Figures and Examples:

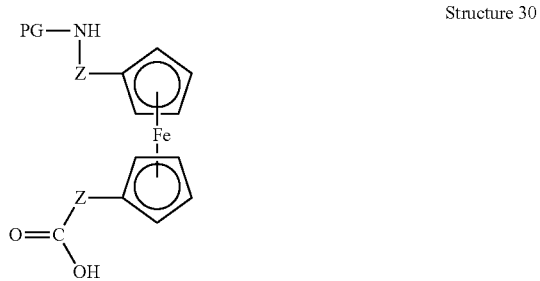

Structure 30

In Structure 30, the PG protecting group is suitable for use in peptide nucleic acid synthesis, with MMT, boc and Fmoc being preferred.

These same intermediate compounds can be used to form ETM or metallocene polymers, which are added to the nucleic acids, rather than as backbone replacements, as is more fully described below.

In a preferred embodiment, the ETMs are attached as polymers, for example as metallocene polymers, in a "branched" configuration similar to the "branched DNA" embodiments herein and as outlined in U.S. Pat. No. 5,124,246, using modified functionalized nucleotides. The general idea is as follows. A modified phosphoramidite nucleotide is generated that can ultimately contain a free hydroxy group that can be used in the attachment of phosphoramidite ETMs such as metallocenes. This free hydroxy group could be on the base or the backbone, such as the ribose or the phosphate (although as will be appreciated by those in the art, nucleic acid analogs containing other structures can also be used). The modified nucleotide is incorporated into a nucleic acid, and any hydroxy protecting groups are removed, thus leaving the free hydroxyl. Upon the addition of a phosphoramidite ETM such as a metallocene, as described above in the Structures, ETMs, such as metallocene ETMs, are added. Additional phosphoramidite ETMs such as metallocenes can be added, to form "ETM polymers", including "metallocene polymers" as depicted herein, particularly for ferrocene. In addition, in some embodiments, it is desirable to increase the solubility of the polymers by adding a "capping" group to the terminal ETM in the polymer, for example a final phosphate group to the metallocene as is generally depicted in FIG. 4. Other suitable solubility enhancing "capping" groups will be appreciated by those in the art. It should be noted that these solubility enhancing groups can be added to the polymers in other places, including to the ligand rings, for example on the metallocenes as discussed herein.

A preferred embodiment of this general idea is outlined in the Figures. In this embodiment, the 2' position of a ribose of a phosphoramidite nucleotide is first functionalized to contain a protected hydroxy group, in this case via an oxo-linkage, although any number of linkers can be used, as is generally described herein for Z linkers. The protected modified nucleotide is then incorporated via standard phosphoramidite chemistry into a growing nucleic acid. The protecting group is removed, and the free hydroxy group is used, again using standard phosphoramidite chemistry to add a phosphoramidite metallocene such as ferrocene. A similar reaction is possible for nucleic acid analogs. For example, using peptide nucleic acids and the metallocene monomer shown in Structure 30, peptide nucleic acid structures containing metallocene polymers could be generated.

Figure 3B:
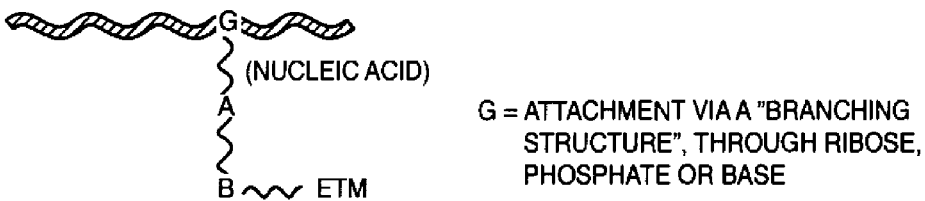

Thus, the present invention provides recruitment linkers of nucleic acids comprising "branches" of metallocene polymers as is generally depicted in FIGS. 3, 4 and 5. Preferred embodiments also utilize metallocene polymers from one to about 50 metallocenes in length, with from about 5 to about 20 being preferred and from about 5 to about 10 being especially preferred.

In addition, when the recruitment linker is nucleic acid, any combination of ETM attachments may be done.

In a preferred embodiment, the recruitment linker is not nucleic acid, and instead may be any sort of linker or polymer. As will be appreciated by those in the art, generally any linker or polymer that can be modified to contain ETMs can be used. In general, the polymers or linkers should be reasonably soluble and contain suitable functional groups for the addition of ETMs.

As used herein, a "recruitment polymer" comprises at least two or three subunits, which are covalently attached. At least some portion of the monomeric subunits contain functional groups for the covalent attachment of ETMs. In some embodiments coupling moieties are used to covalently link the subunits with the ETMs. Preferred functional groups for attachment are amino groups, carboxy groups, oxo groups and thiol groups, with amino groups being particularly preferred. As will be appreciated by those in the art, a wide variety of recruitment polymers are possible.

Suitable linkers include, but are not limited to, alkyl linkers (including heteroalkyl (including (poly)ethylene glycol-type structures), substituted alkyl, aryalkyl linkers, etc. As above for the polymers, the linkers will comprise one or more functional groups for the attachment of ETMs, which will be done as will be appreciated by those in the art, for example through the use homo- or hetero-bifunctional linkers as are well known (see 1994 Pierce Chemical Company catalog, technical section on cross-linkers, pages 155-200, incorporated herein by reference).

Suitable recruitment polymers include, but are not limited to, functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

In a preferred embodiment, the recruitment linker comprises a metallocene polymer, as is described above.

When non-nucleic acid recruitment linkers are used, attachment of the linker/polymer of the recruitment linker will be done generally using standard chemical techniques, such as will be appreciated by those in the art. For example, when alkyl-based linkers are used, attachment can be similar to the attachment of insulators to nucleic acids.

In addition, it is possible to have recruitment linkers that are mixtures of nucleic acids and non-nucleic acids, either in a linear form (i.e. nucleic acid segments linked together with alkyl linkers) or in branched forms (nucleic acids with alkyl "branches" that may contain ETMs and may be additionally branched).

In a preferred embodiment, it is the target sequence itself that carries the ETMs. For example, as is more fully described below, it is possible to enzymatically add triphosphate nucleotides comprising the ETMs of the invention to a growing nucleic acid, for example during a polymerase chain reaction (PCR). As will be recognized by those in the art, while several enzymes have been shown to generally tolerate modified nucleotides, some of the modified nucleotides of the invention, for example the "nucleoside replacement" embodiments and putatively some of the phosphate attachments, may or may not be recognized by the enzymes to allow incorporation into a growing nucleic acid. Therefore, preferred attachments in this embodiment are to the base or ribose of the nucleotide.

Thus, for example, PCR amplification of a target sequence, as is well known in the art, will result in target sequences comprising ETMs, generally randomly incorporated into the sequence. The system of the invention can then be configured to allow detection using these ETMs.

Alternatively, as outlined more fully below, it is possible to enzymatically add nucleotides comprising ETMs to the terminus of a nucleic acid, for example a target nucleic acid. In this embodiment, an effective "recruitment linker" is added to the terminus of the target sequence, that can then be used for detection.

In some embodiments, when the recruitment linker is nucleic acid, it may be desirable in some instances to have some or all of the recruitment linker be double stranded. In one embodiment, there may be a second recruitment linker, substantially complementary to the first recruitment linker, that can hybridize to the first recruitment linker. In a preferred embodiment, the first recruitment linker comprises the covalently attached ETMs. In an alternative embodiment, the second recruitment linker contains the ETMs, and the first recruitment linker does not, and the ETMs are recruited to the surface by hybridization of the second recruitment linker to the first. In yet another embodiment, both the first and second recruitment linkers comprise ETMs. It should be noted, as discussed above, that nucleic acids comprising a large number of ETMs may not hybridize as well, i.e. the $T_m$ may be decreased, depending on the site of attachment and the characteristics of the ETM. Thus, in general, when multiple ETMs are used on hybridizing strands, generally there are less than about 5, with less than about 3 being preferred, or alternatively the ETMs should be spaced sufficiently far apart that the intervening nucleotides can sufficiently hybridize to allow good kinetics.

In a preferred embodiment, the reporter particle does not comprise directly attached ETMs. Rather, the reporter particle comprises two different components: a capture binding partner (used to bind to the assay complex) and at least one amplification sequences, to which label probes will bind. This embodiment is generally depicted in FIG. 2H.

In this embodiment, the reporter particle comprises a capture binding partner as outlined above. In addition; the reporter particle comprises nucleic acid probes comprising amplification sequences, to which label probes can bind. Again, for each of these, binding may be direct or indirect. An "amplification sequence" or "amplification segment" or grammatical equivalents herein is meant a sequence that is used, either directly or indirectly, to bind to a first portion of a label probe; the label probe comprises the ETMs. Preferably, the reporter particle comprises a multiplicity of amplification sequences.

The amplification sequences of the amplifier probe are used, either directly or indirectly, to bind to a label probe to allow detection. In a preferred embodiment, the amplification sequences of the amplifier probe are substantially complementary to a first portion of a label probe. Alternatively, amplifier extender probes are used, that have a first portion that binds to the amplification sequence and a second portion that binds to the first portion of the label probe.

Thus, label probes are either substantially complementary to an amplification sequence or to a portion of the target sequence. Accordingly, the label probes can be configured in a variety of ways, as is generally described herein, depending on whether a "mechanism-1" or "mechanism-2" detection system is utilized, as described below.

In a preferred embodiment, the reporter particle further comprises a SAM, as is outlined above for the transport particle and/or electrode. In general, this is a mixed monolayer comprising one, two, three or four components, as outlined above for electrodes and/or transport particles.

The transport moiety and the reporter composition may be added together in a wide variety of ratios, depending on the composition of the moieties (for example, whether they are both particles), the relative size of the moieties, the density of the binding partners on the particles, etc. For example, when a magnetic first particle is used and a colloid particle as the reporter particle, the reporter particles are generally added in excess. What is important is that neither the transport composition nor the reporter composition is added in such excess that a single type of particle or composition will carry all the target analytes; the ratios are important to allow both the transport and reporter compositions to bind. However, in general, depending on the size of the particles, generally an excess of reporter particles are added, particularly when large magnetic particles are used with smaller reporter particles.

Accordingly, the methods of the invention provide for the detection of target analytes in a test sample. In general, the sample is added to the compositions of the invention comprising transport and reporter compositions. The sample is added to the compositions under conditions whereby the target analyte, if present, can bind to the first and second binding ligands to form an assay complex. "Assay complex" herein is meant the collection of moieties, including the target analyte and the binding ligands that contains at least one ETM and thus allows detection. The composition of the assay complex depends on the use of the different components outlined herein. The assay complex is then transported to the electrode surface, comprising the conductive oligomers, and the presence or absence of the ETMs is detected.

Transport of the assay complex using the transport composition may be done in a wide variety of ways, as will be appreciated by those in the art, and will depend in part on the components of the system. Thus, for example, when magnetic particles are used as the transport particles, the application of a magnetic field to bring the assay complexes and extra magnetic transport particles to the surface can be done. When the transport particles are not magnetic, transport can proceed via physical aggregation of the assay complexes with gravitational settling of the assay complexes on the electrode. Alternate transport mechanisms include, but are not limited to, electrophoretic transport of the assay complexes, centrifugation, etc. It should be noted that the use of different sized colloids may allow the use of differential electrophoretic transport based on different charge densities; that is, when a larger transport particle is used with smaller (charged) reporter particles, i.e. the transport particle can be "covered" or "coated" with the smaller particles, and thus the charge densities of the transport particle and the assay complex will allow differential electrophoretic transport.

Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Once the assay complexes of the invention are made, that minimally comprise a target analyte and at least one ETM, detection proceeds with electronic initiation. Without being limited by the mechanism or theory, detection is based on the transfer of electrons from the ETM to the electrode.

Detection of electron transfer, i.e. the presence of the ETMs, is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the conductive oligomer used, the composition and integrity of the monolayer, and what type of reference electrode is used. As described herein, ferrocene is a preferred ETM.

Once the assay complexes of the invention are made, that minimally comprise a target sequence and a label probe, detection proceeds with electronic initiation. Without being limited by the mechanism or theory, detection is based on the transfer of electrons from the ETM to the electrode.

Detection of electron transfer, i.e. the presence of the ETMs, is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the conductive oligomer used, the composition and integrity of the monolayer, and what type of reference electrode is used. As described herein; ferrocene is a preferred ETM.

In a preferred embodiment, a co-reductant or co-oxidant (collectively, co-redoxant) is used, as an additional electron source or sink. See generally Sato et al., Bull. Chem. Soc. Jpn 66:1032 (1993); Uosaki et al., Electrochimica Acta 36:1799 (1991); and Alleman et al., J. Phys. Chem. 100:17050 (1996); all of which are incorporated by reference.

In a preferred embodiment, an input electron source in solution is used in the initiation of electron transfer, preferably when initiation and detection are being done using DC current or at AC frequencies where diffusion is not limiting. In general, as will be appreciated by those in the art, preferred embodiments utilize monolayers that contain a minimum of "holes", such that short-circuiting of the system is avoided. This may be done in several general ways. In a preferred embodiment, an input electron source is used that has a lower or similar redox potential than the ETM of the label probe. Thus, at voltages above the redox potential of the input electron source, both the ETM and the input electron source are oxidized and can thus donate electrons; the ETM donates an electron to the electrode and the input source donates to the ETM. For example, ferrocene, as a ETM attached to the compositions of the invention as described in the examples, has a redox potential of roughly 200 mV in aqueous solution (which can change significantly depending on what the ferrocene is bound to, the manner of the linkage and the presence of any substitution groups). Ferrocyanide, an electron source, has a redox potential of roughly 200 mV as well (in aqueous solution). Accordingly, at or above voltages of roughly 200 mV, ferrocene is converted to ferricenium, which then transfers an electron to the electrode. Now the ferricyanide can be oxidized to transfer an electron to the ETM. In this way, the electron source (or co-reductant) serves to amplify the signal generated in the system, as the electron source molecules rapidly and repeatedly donate electrons to the ETM attached to the nucleic acid. The rate of electron donation or acceptance will be limited by the rate of diffusion of the co-reductant, the electron transfer between the co-reductant and the ETM, which in turn is affected by the concentration and size, etc.

Alternatively, input electron sources that have lower redox potentials than the ETM are used. At voltages less than the redox potential of the ETM, but higher than the redox potential of the electron source, the input source such as ferrocyanide is unable to be oxidized and thus is unable to donate an electron to the ETM; i.e. no electron transfer occurs. Once ferrocene is oxidized, then there is a pathway for electron transfer.

In an alternate preferred embodiment, an input electron source is used that has a higher redox potential than the ETM of the label probe. For example, luminol, an electron source, has a redox potential of roughly 720 mV. At voltages higher than the redox potential of the ETM, but lower than the redox potential of the electron source, i.e. 200-720 mV, the ferrocene is oxidized, and transfers a single electron to the electrode via the conductive oligomer. However, the ETM is unable to accept any electrons from the luminol electron source, since the voltages are less than the redox potential of the luminol. However, at or above the redox potential of luminol, the luminol then transfers an electron to the ETM, allowing rapid and repeated electron transfer. In this way, the electron source (or co-reductant) serves to amplify the signal generated in the system, as the electron source molecules rapidly and repeatedly donate electrons to the ETM of the label probe.

Luminol has the added benefit of becoming a chemiluminiscent species upon oxidation (see Jirka et al., Analytica Chimica Acta 284:345 (1993)), thus allowing photo-detection of electron transfer from the ETM to the electrode. Thus, as long as the luminol is unable to contact the electrode directly, i.e. in the presence of the SAM such that there is no efficient electron transfer pathway to the electrode, luminol can only be oxidized by transferring an electron to the ETM on the label probe. When the ETM is not present, i.e. when the target sequence is not hybridized to the composition of the invention, luminol is not significantly oxidized, resulting in a low photon emission and thus a low (if any) signal from the luminol. In the presence of the target, a much larger signal is generated. Thus, the measure of luminol oxidation by photon emission is an indirect measurement of the ability of the ETM to donate electrons to the electrode. Furthermore, since photon detection is generally more sensitive than electronic detection, the sensitivity of the system may be increased. Initial results suggest that luminescence may depend on hydrogen peroxide concentration, pH, and luminol concentration, the latter of which appears to be non-linear.

Suitable electron source molecules are well known in the art, and include, but are not limited to, ferricyanide, and luminol.

Alternatively, output electron acceptors or sinks could be used, i.e. the above reactions could be run in reverse, with the ETM such as a metallocene receiving an electron from the electrode, converting it to the metallicenium; with the output electron acceptor then accepting the electron rapidly and repeatedly. In this embodiment, cobalticenium is the preferred ETM.

The presence of the ETMs at the surface of the monolayer can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance and impedence. These methods include time or frequency dependent methods based on AC or DC currents, pulsed methods, lock-in techniques, filtering (high pass, low pass, band pass), and time-resolved techniques including time-resolved fluoroscence.

In one embodiment, the efficient transfer of electrons from the ETM to the electrode results in stereotyped changes in the redox state of the ETM. With many ETMs including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp 197-202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include $Ru(NH_3)_4py$ and $Ru(bpy)_2im$ as preferred examples. It should be understood that only the donor or acceptor that is being monitored by absorbance need have ideal spectral characteristics.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with $Ru(4,7-biphenyl_2-phenanthroline)_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85-277, 1988). Preferred examples display efficient fluorescence (reasonably high quantum yields) as well as low reorganization energies. These include $Ru(4,7-biphenyl_2-phenanthroline)_3^{2+}$, $Ru(4,4'-diphenyl-2,2'-bipyridine)_3^{2+}$ and platinum complexes (see Cummings et al., J. Am. Chem. Sob. 118:1949-1960 (1996), incorporated by reference). Alternatively, a reduction in fluorescence associated with hybridization can be measured using these systems.

In a further embodiment, electrochemiluminescence is used as the basis of the electron transfer detection. With some ETMs such as $Ru^{2+}(bpy)_3$, direct luminescence accompanies excited state decay. Changes in this property are associated with nucleic acid hybridization and can be monitored with a simple photomultiplier tube arrangement (see. Blackburn, G. F. Clin. Chem. 37: 1534-1539 (1991); and Juris et al., supra.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators (such as resistance) and of conductors (such as conductivity, impedance and capicitance) could be used to monitor electron transfer between ETM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In a preferred embodiment, electron transfer is initiated using alternating current (AC) methods. Without being bound by theory, it appears that ETMs, bound to an electrode, generally respond similarly to an AC voltage across a circuit containing resistors and capacitors. Basically, any methods which enable the determination of the nature of these complexes, which act as a resistor and capacitor, can be used as the basis of detection. Surprisingly, traditional electrochemical theory, such as exemplified in Laviron et al., J. Electroanal. Chem. 97:135 (1979) and Laviron et al., J. Electroanal. Chem. 105:35 (1979), both of which are incorporated by reference, do not accurately model the systems described herein, except for very small $E_{AC}$ (less than 10 mV) and relatively large numbers of molecules. That is, the AC current (1) is not accurately described by Laviron's equation. This may be due in part to the fact that this theory assumes an unlimited source and sink of electrons, which is not true in the present systems.

The AC voltametry theory that models these systems well is outlined in O'Connor et al., J. Electroanal. Chem. 466(2): 197-202 (1999), hereby expressly incorporated by reference. The equation that predicts these systems is shown below as Equation 1:

$$i_{avg} = 2nfFN_{total} \cdot \frac{\sinh\left[\frac{nF}{RT} \cdot E_{AC}\right]}{\cosh\left[\frac{nF}{RT} \cdot E_{AC}\right] + \cosh\left[\frac{nF}{RT}(E_{DC} - E_O)\right]} \quad \text{Equation 1}$$

In Equation 1, n is the number of electrons oxidized or reduced per redox molecule, f is the applied frequency, F is Faraday's constant, $N_{total}$ is the total number of redox molecules, $E_O$ is the formal potential of the redox molecule, R is the gas constant, T is the temperature in degrees Kelvin, and $E_{DC}$ is the electrode potential. The model fits the experimental data very well. In some cases the current is smaller than predicted, however this has been shown to be caused by ferrocene degradation which may be remedied in a number of ways.

In addition, the faradaic current can also be expressed as a function of time, as shown in Equation 2:

$$I_f(t) = \frac{q_e N_{total} nF}{2RT\left(\cosh\left[\frac{nF}{RT}(V(t) - E_0)\right] + 1\right)} \cdot \frac{dV(t)}{dt} \quad \text{Equation 2}$$

$I_F$ is the Faradaic current and $q_e$ is the elementary charge.

However, Equation 1 does not incorporate the effect of electron transfer rate nor of instrument factors. Electron transfer rate is important when the rate is close to or lower than the applied frequency. Thus, the true $i_{AC}$ should be a function of all three, as depicted in Equation 3.

$$i_{AC} = f(\text{Nernst factors}) f(k_{ET}) f(\text{instrument factors}) \quad \text{Equation 3}$$

These equations can be used to model and predict the expected AC currents in systems which use input signals comprising both AC and DC components. As outlined above, traditional theory surprisingly does not model these systems at all, except for very low voltages.

In general, non-specifically bound label probes/ETMs show differences in impedance (i.e. higher impedances) than when the label probes containing the ETMs are specifically bound in the correct orientation. In a preferred embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of ETM-containing probes and target-specific assay complex formation may be monitored.

Accordingly, when using AC initiation and detection methods, the frequency response of the system changes as a result of the presence of the ETM. By "frequency response" herein is meant a modification of signals as a result of electron transfer between the electrode and the ETM. This modification is different depending on signal frequency. A frequency response includes AC currents at one or more frequencies, phase shifts, DC offset voltages, faradaic impedance, etc.

Once the assay complex including the target sequence and label probe is made, a first input electrical signal is then applied to the system, preferably via at least the sample electrode (containing the complexes of the invention) and the counter electrode, to initiate electron transfer between the electrode and the ETM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 100 MHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In a preferred embodiment, the first input signal comprises a DC component and an AC component. That is, a DC offset voltage between the sample and counter electrodes is swept through the electrochemical potential of the ETM (for example, when ferrocene is used, the sweep is generally from 0 to 500 mV) (or alternatively, the working electrode is grounded and the reference electrode is swept from 0 to −500 mV). The sweep is used to identify the DC voltage at which the maximum response of the system is seen. This is generally at or about the electrochemical potential of the ETM. Once this voltage is determined, either a sweep or one or more uniform DC offset voltages may be used: DC offset voltages of from about −1 V to about +1.1 V are preferred, with from about −500 mV to about +800 mV being especially preferred, and from about −300 mV to about 500 mV being particularly preferred. In a preferred embodiment, the DC offset voltage is not zero. On top of the DC offset voltage, an AC signal component of variable amplitude and frequency is applied. If the ETM is present, and can respond to the AC perturbation, an AC current will be produced due to electron transfer between the electrode and the ETM.

For defined systems, it may be sufficient to apply a single input signal to differentiate between the presence and absence of the ETM (i.e. the presence of the target sequence) nucleic acid. Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are used, although as outlined above, DC voltage sweeps are preferred. This may be done at a single frequency, or at two or more frequencies.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as those that do not possess optimal spacing configurations.

In a preferred embodiment, measurements of the system are taken at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the ETM, higher frequencies result in a loss or decrease of output signal. At some point, the frequency will be greater than the rate of electron transfer between the ETM and the electrode, and then the output signal will also drop.

In one embodiment, detection utilizes a single measurement of output signal at a single frequency. That is, the frequency response of the system in the absence of target sequence, and thus the absence of label probe containing ETMs, can be previously determined to be very low at a particular high frequency. Using this information, any response at a particular frequency, will show the presence of the assay complex. That is, any response at a particular frequency is characteristic of the assay complex. Thus, it may only be necessary to use a single input high frequency, and any changes in frequency response is an indication that the ETM is present, and thus that the target sequence is present.

In addition, the use of AC techniques allows the significant reduction of background signals at any single frequency due to entities other than the ETMs, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, i.e. have partial or insufficient monolayers, i.e. where the solvent is accessible to the electrode. As outlined above, in DC techniques, the presence of "holes" where the electrode is accessible to the solvent can result in solvent charge carriers "short circuiting" the system, i.e. the reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at least two separate frequencies, with measurements at a plurality of frequencies being preferred. A plurality of frequencies includes a scan. For example, measuring the output signal, e.g., the AC current, at a low input frequency such as 1-20 Hz, and comparing the response to the output signal at high frequency such as 10-100 kHz will show a frequency response difference between the presence and absence of the ETM. In a preferred embodiment, the frequency response is determined at least two, preferably at least about five, and more preferably at least about ten frequencies.

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the ETM; the solvent; and the type and concentration of salt. At a given input signal, the presence and magnitude of the output signal will depend in general on the presence or absence of the ETM, the placement and distance of the ETM from the surface of the monolayer and the character of the input signal. In some embodiments, it may be possible to distinguish between non-specific binding of label probes and the formation of target specific assay complexes containing label probes, on the basis of impedance.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femptoamp to about 1 milliamp, with currents from about 50 femptoamps to about 100 microamps being preferred, and from about 1 picoamp to about 1 microamp being especially preferred.

In a preferred embodiment, the output signal is phase shifted in the AC component relative to the input signal. Without being bound by theory, it appears that the systems of the present invention may be sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between the presence and absence of the ETM, and/or differences between the presence of target-specific assay complexes comprising label probes and non-specific binding of the label probes to the system components.

The output signal is characteristic of the presence of the ETM; that is, the output signal is characteristic of the presence of the target-specific assay complex comprising label probes and ETMs. In a preferred embodiment, the basis of the detection is a difference in the faradaic impedance of the system as a result of the formation of the assay complex. Faradaic impedance is the impedance of the system between the electrode and the ETM. Faradaic impedance is quite different from the bulk or dielectric impedance, which is the impedance of the bulk solution between the electrodes. Many factors may change the faradaic impedance which may not effect the bulk impedance, and vice versa. Thus, the assay complexes comprising the nucleic acids in this system have a certain faradaic impedance, that will depend on the distance between the ETM and the electrode, their electronic properties, and the composition of the intervening medium, among other things. Of importance in the methods of the invention is that the faradaic impedance between the ETM and the electrode is signficantly different depending on whether the label probes containing the ETMs are specifically or non-specifically bound to the electrode.

Accordingly, the present invention further provides apparatus for the detection of nucleic acids using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In a preferred embodiment, the first measuring electrode comprises a single stranded nucleic acid capture probe covalently attached via an attachment linker, and a monolayer comprising conductive oligomers, such as are described herein.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target nucleic acid.

Thus, the compositions of the present invention may be used in a variety of research, clinical, quality control, or field testing settings.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected, for example using ribosomal RNA (rRNA) as the target sequences.

In a preferred embodiment, the nucleic acids of the invention find use as probes for toxic bacteria in the screening of water and food samples. For example, samples may be treated to lyse the bacteria to release its nucleic acid (particularly rRNA), and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

Thus, the present invention provides for extremely specific and sensitive probes, which may, in some embodiments, detect target sequences without removal of unhybridized probe. This will be useful in the generation of automated gene probe assays.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a ETM, covalently attached to an electrode via a conductive oligomer with subsequent detection of the target sequence. Alternatively, PCR is done using nucleotides labelled with a ETM, either in the presence of, or with subsequent addition to, an electrode with a conductive oligomer and a target nucleic acid. Binding of the PCR product containing ETMs to the electrode composition will allow detection via electron transfer. Finally, the nucleic acid attached to the electrode via a conductive polymer may be one PCR primer, with addition of a second primer labelled with an ETM. Elongation results in double stranded nucleic acid with a ETM and electrode covalently attached. In this way, the present invention is used for PCR detection of target sequences.

In a preferred embodiment, the arrays are used for mRNA detection. A preferred embodiment utilizes either capture probes or capture extender probes that hybridize close to the 3' polyadenylation tail of the mRNAs. This allows the use of one species of target binding probe for detection, i.e. the probe contains a poly-T portion that will bind to the poly-A tail of the mRNA target. Generally, the probe will contain a second portion, preferably non-poly-T, that will bind to the detection probe (or other probe). This allows one target-binding probe to be made, and thus decreases the amount of different probe synthesis that is done.

In a preferred embodiment, the use of restriction enzymes and ligation methods allows the creation of "universal" arrays. In this embodiment, monolayers comprising capture probes that comprise restriction endonuclease ends, as is generally depicted in FIG. 7 of PCT US97/20014 (now WO 98/20162). By utilizing complementary portions of nucleic acid, while leaving "sticky ends", an array comprising any number of restriction endonuclease sites is made. Treating a target sample with one or more of these restriction endonucleases allows the targets to bind to the array. This can be done without knowing the sequence of the target. The target sequences can be ligated, as desired, using standard methods such as ligases, and the target sequence detected, using either standard labels or the methods of the invention.

The present invention provides methods which can result in sensitive detection of nucleic acids. In a preferred embodiment, less than about $10 \times 10^6$ molecules are detected, with less than about $10 \times 10^5$ being preferred, less than $10 \times 10^4$ being particularly preferred, less than about $10 \times 10^3$ being especially preferred, and less than about $10 \times 10^2$ being most preferred. As will be appreciated by those in the art, this assumes a 1:1 correlation between target sequences and reporter molecules; if more than one reporter molecule (i.e. electron transfer Moeity) is used for each target sequence, the sensitivity will go up.

All references cited herein are incorporated by reference in their entirety.

We claim:

1. A composition comprising:
   a) a magnetic particle comprising a first binding ligand that specifically binds a target analyte; and
   b) a colloidal particle comprising:
      i) a second binding ligand that specifically binds said target analyte; and
      ii) a third binding ligand different from said second binding ligand,
   wherein said first and second binding ligands are antibodies, and said third binding ligand is a nucleic acid.

2. The composition according to claim 1 wherein said composition further comprises an array comprising a fourth binding ligand.

3. The composition according to claim 1 wherein said colloidal particle comprises Au.

4. A kit comprising the composition of claim 1.

* * * * *